United States Patent
Boger

(10) Patent No.: US 9,586,974 B2
(45) Date of Patent: Mar. 7, 2017

(54) CYCLIC N-ACYL O-AMINO PHENOL CBI DERIVATIVE

(71) Applicants: THE SCRIPPS RESEARCH LINSTITUTE, La Jolla, CA (US); Dale L. Boger, La Jolla, CA (US)

(72) Inventor: Dale Boger, Lajolla, CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 14/773,257

(22) PCT Filed: Mar. 20, 2014

(86) PCT No.: PCT/US2014/031338
§ 371 (c)(1),
(2) Date: Sep. 4, 2015

(87) PCT Pub. No.: WO2014/160586
PCT Pub. Date: Oct. 2, 2014

(65) Prior Publication Data
US 2016/0016972 A1    Jan. 21, 2016

Related U.S. Application Data

(60) Provisional application No. 61/806,212, filed on Mar. 28, 2013.

(51) Int. Cl.
*C07D 498/06* (2006.01)
*A61K 31/5365* (2006.01)
*C07D 519/00* (2006.01)

(52) U.S. Cl.
CPC ........ *C07D 498/06* (2013.01); *A61K 31/5365* (2013.01); *C07D 519/00* (2013.01)

(58) Field of Classification Search
None
See application file for complete search history.

(56) References Cited

U.S. PATENT DOCUMENTS

2004/0002528 A1    1/2004    Boger
2011/0112163 A1    5/2011    Boger

OTHER PUBLICATIONS

MeSH headings for "proliferative" (retrieved from http://www.ncbi.nlm.nih.gov/mesh on May 20, 2016).*
Tepe, Tetrahedron 58, 3553-59 (2002).*
Boger et al., *Bioorg Med Chem*, (11, 1995) 3(11):1429-1453.
International Search Report for PCT/US2014/031338 (WO 2014160586).
Wolfe et al., *J Med Chem* (Apr. 29, 2013) 4104-4115.

* cited by examiner

*Primary Examiner* — Theodore R West
(74) *Attorney, Agent, or Firm* — Husch Blackwell LLP

(57) ABSTRACT

A group of cyclic N-acyl O-amino phenol CBI derivatives were synthesized and shown to be pro-drugs, subject to reductive activation by cleavage of a N-0 bond, effectively releasing the free drug in functional in vitro cellular assays for cytotoxic activity approaching the activity of the free drug, yet remain essentially stable to ex vivo DNA alkylation conditions. Assessment of the in vivo antitumor activity of a representative pro-drug indicates that a contemplated pro-drug approaches the potency and exceeds the efficacy of the free drug itself (CBI-indole$_2$), indicating that the inactive pro-drugs not only effectively release the free drug in vivo, but that they offer additional advantages related to a controlled or targeted release in vivo.

11 Claims, 5 Drawing Sheets

CYCLIC N-ACYL O-AMINO PHENOL CBI DERIVATIVE

CROSS-REFERENCE TO RELATED APPLICATION

This application claims priority from provisional application No. 61/806,212, filed Mar. 28, 2013.

GOVERNMENTAL SUPPORT

The present invention was made with governmental support pursuant to grant CA41986 from the National Institutes of Health/National Cancer Institute. The government has certain rights in the invention.

FIELD OF INVENTION

The invention relates to pro-drug anticancer agents and to their use. More particularly, the invention relates to cyclic N-acyl O-amino phenol pro-drugs of CBI-TMI and CBI-indole$_2$.

BACKGROUND ART

Duocarmycin SA (Compound 1) [Ichimura et al., *J. Antibiot.* 1990, 43:1037-1038] and CC-1065 (Compound 2) [Martin et al., *J. Antibiot.* 1981, 34:1119-1125], below, are the two most widely

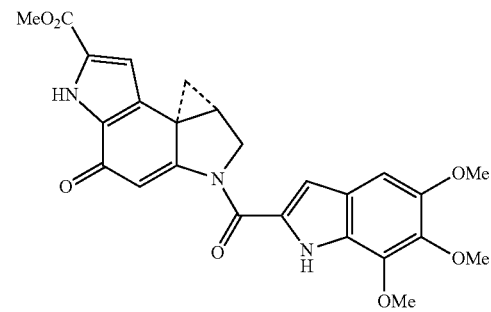

(+)-Duocarmycin SA

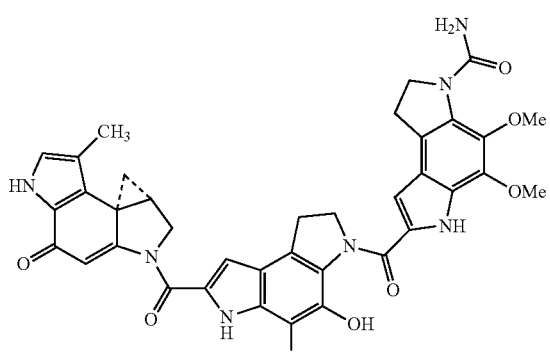

(+)-CC-1065 recognized members of a class of exceptionally potent naturally occurring antitumor agents that also include duocarmycin A [Takahashi et al., *J. Antibiot.* 1988, 41:1915-1917], yatakemycin [Igarashi et al., *J. Antibiot.* 2003, 56:107-113](below).

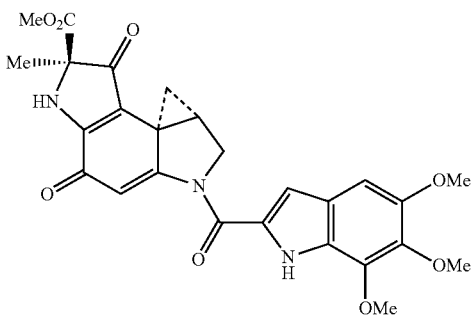

(+)-Duocarmycin A

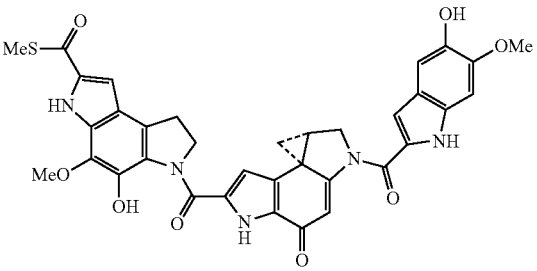

(+)-Yatakemycin

This unique class of natural products derives its antitumor properties from their ability to alkylate DNA in a sequence selective manner. [For duocarmycin SA, see: (a) Boger et al., *J. Am. Chem. Soc.* 1994, 116:1635-1656; for yatakemycin, see: (b) Parrish et al., *J. Am. Chem. Soc.* 2003, 125:10971-10976; (c) Trzupek et al., *Nat. Chem. Biol.* 2006, 2:79-82; (d) Tichenor et al., *J. Am. Chem. Soc.* 2007, 129:10858-10869; for CC-1065, see: (e) Hurley et al., *Biochemistry* 1988, 27:3886-3892; (f) Boger et al., *Bioorg. Med. Chem.* 1994, 2:115-135; (g) Boger et al., *J. Am. Chem. Soc.* 1991, 113:3980-3983; (h) Boger et al., *Proc. Nat. Acad. Sci. U.S.A.* 1991, 88:1431-1435; (i) Boger et al., *J. Am. Chem. Soc.* 1990, 112:4623-4632; (j) Boger et al., *J. Am. Chem. Soc.* 1991, 113:3980-3983; for duocarmycin A, see: (k) Boger et al., *J. Am. Chem. Soc.* 1990, 112:8961-8971; (l) Boger et al., *J. Am. Chem. Soc.* 1991, 113:6645-6649; (m) Boger et al., *Med. Chem. Lett.* 1992, 2:759-765. (n) Boger et al., *J. Am. Chem. Soc.* 1993, 115:9872-9873; (o) Boger et al., *Chem.-Biol. Interactions* 1990, 73:29-52. Reviews: (a) Boger et al., *Angew. Chem., Int. Ed. Engl.* 1996, 35:1438-1474; (b) Boger et al., *Acc. Chem. Res.* 1995, 28:20-29; (c) Boger et al., *Proc. Natl. Acad. Sci. U.S.A.* 1995, 92:3642-3649; (d) Boger et al., *Acc. Chem. Res.* 1999, 32:1043-1052; (e) Tichenor et al., *Natural Prod. Rep.* 2008, 25:220-226; (f) MacMillan et al., *J. Med. Chem.* 2009, 52:5771-5780; (g) Searcey et al., *Curr. Pharm. Des.* 2002, 8:1375-1389; and (h) Tse et al., *Chem. Biol.* 2004, 11:1607-1617.]

In depth studies of the natural products, their synthetic unnatural enantiomers, [(a) Boger et al., *J. Am. Chem. Soc.* 1988, 110:1321-1323; (b) Boger et al., *J. Am. Chem. Soc.* 1988, 110:4796-4807; (c) Boger et al., *J. Am. Chem. Soc.* 1992, 114:10056-10058; (d) Boger et al., *J. Am. Chem. Soc.* 1993, 115:925-9036. (e) Boger et al., *J. Am. Chem. Soc.* 1996, 118:2301-2302; (f) Boger et al., *J. Am. Chem. Soc.* 1997, 119:311-325; (g) Boger et al., *Chem. Rev.* 1997, 97:787-828; (h) Tichenor et al., *J. Am. Chem. Soc.* 2004, 126:8396-8398; (i) Tichenor et al., *J. Am. Chem. Soc.* 2006, 128:15683-15696; (j) MacMillan et al., *J. Am. Chem. Soc.* 2009, 131:1187-1194.] and key analogues have defined many of the fundamental features that control their DNA alkylation selectivity, efficiency, and catalysis, resulting in a detailed understanding of the relationships between structure, reactivity, and biological activity. [See the citations above and (a) Boger et al., *J. Am. Chem. Soc.* 1997, 119:4977-4986; (b) Boger et al., *J. Am. Chem. Soc.* 1997, 119:4987-4998; (c) Boger et al., *Bioorg. Med. Chem.* 1997, 5:263-276.]

CBI (1,2,9,9a-tetrahydrocyclopropa[c]benz-[e]indol-4-one), below, is one of the most

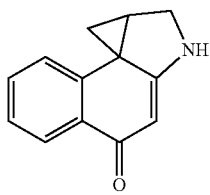

CBI studied synthetic analogues of the duocarmycin family since the inventor and co-workers first introduced it in 1989. [(a) Boger et al., *J. Am. Chem. Soc.* 1989, 111:6461-6463; (b) Boger et al., *J. Org. Chem.* 1990, 55:5823-5832; (c) Boger et al., *Tetrahedron Lett.* 1990, 31:793-796; (d) Boger et al., *Bioorg. Med. Chem. Lett.* 1991, 1:55-58; (e) Boger et al., *J. Am. Chem. Soc.* 1992, 114:5487-5496; (f) Boger et al., *J. Am. Chem. Soc.* 1994, 116:5523-5524; (g) Boger et al., *Bioorg. Med. Chem.* 1995, 3:761-775; (h) Boger et al., *J. Am. Chem. Soc.* 1994, 116:7996-8006; (i) Parrish et al., *Bioorg. Med. Chem.* 2003, 11:3815-3838; (j) Boger et al., *J. Am. Chem. Soc.* 1990, 112:5230-5240.]

The CBI alkylation subunit is not only synthetically more accessible and possesses DNA alkylation properties identical to those of the natural products, [(a) Boger et al., *J. Org. Chem.* 1992, 57:2873-2876; (b) Boger et al., *J. Org. Chem.* 1995, 60:1271-1275; (c) Boger et al., *Synlett* 1997, 515-517; (d) Kastrinsky et al., *J. Org. Chem.* 2004, 69:2284-2289; (e) Lajiness et al., *J. Org. Chem.* 2010, 76:583-587; (f) Drost et al., *J. Org. Chem.* 1991, 56:2240-2244; (g) Aristoff et al., *J. Org. Chem.* 1992, 57:6234-6239; (h) Mohamadi et al., *J. Med. Chem.* 1994, 37:232-239; and (i) Ling et al., *Heterocycl. Commun.* 1997, 3:405-408], but it is also four times more stable and four times more potent than the naturally occurring alkylation subunit of CC-1065 (Compound 2) below, approaching the stability and potency of the duocarmycin SA (Compound 1) alkylation subunit, below. Because the CBI-based

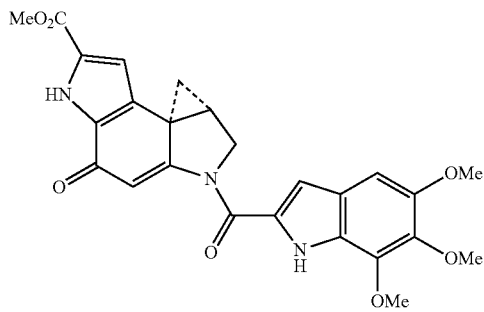

(+)-Duocarmycin SA analogues have also been established to exhibit efficacious in vivo antitumor activity in animal models, it has become an excellent synthetic replacement on which to examine the structure-function features of the natural products, including new pro-drug designs. [(a) Boger et al., *Bioorg. Med. Chem.* 1995, 3:1429-1453; and (b) Boger et al., *Bioorg. Med. Chem. Lett.* 1991, 1:115-120.]

In the course of the early total syntheses [(a) Boger et al., *J. Am. Chem. Soc.* 1988, 110:1321-1323; (b) Boger et al., *J. Am. Chem. Soc.* 1988, 110:4796-4807; (c) Boger et al., *J. Am. Chem. Soc.* 1992, 124:10056-10058; (d) Boger et al., *J. Am. Chem. Soc.* 1993, 115:9025-9036; (e) Boger et al., *J. Am. Chem. Soc.* 1996, 118:2301-2302; (f) Boger et al., *J. Am. Chem. Soc.* 1997, 119:311-325; (g) Boger et al., *Chem. Rev.* 1997, 97; 787-828; (h) Tichenor, M. S.; Kastrinsky et al., *J. Am. Chem. Soc.* 2004, 126; 8396-8398; (i) Tichenor et al., *J. Am. Chem. Soc.* 2006, 128:15683-15696; (j) MacMillan et al., *J. Am. Chem. Soc.* 2009, 131:1187-1194] (noted above) of the natural products and related analogues including CBI-indole$_2$ (Compound 5) below [(a) Boger et al., *Bioorg.*

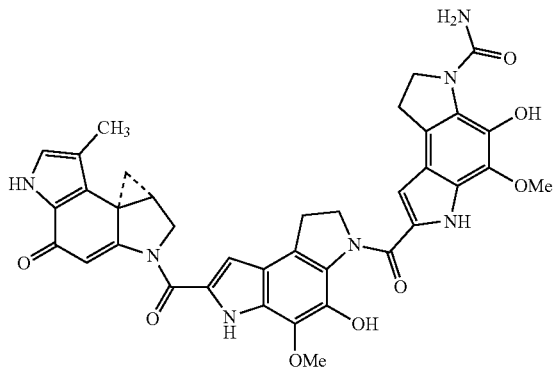

(+)-CC-1065

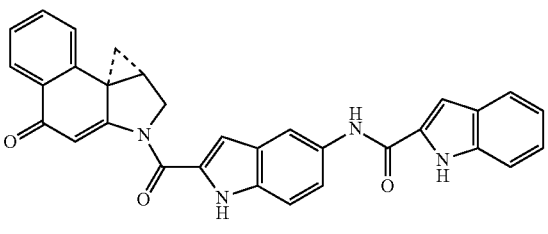

CBI-indole$_2$

*Med. Chem.* 1995, 3:1429-1453; and (b) Boger et al., *Bioorg. Med. Chem. Lett.* 1991, 1:115-120], synthetic phenol precursors such as Compound 4, below, which have yet to undergo the Winstein Ar-3' spiro-

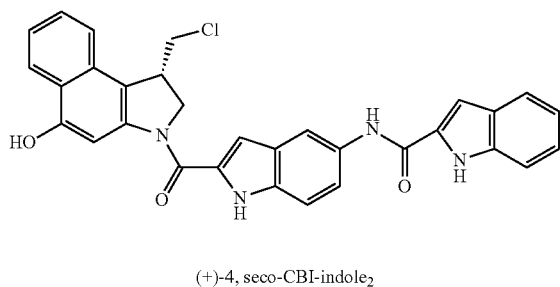

(+)-4, seco-CBI-indole₂ cyclization, were found to be equipotent to and indistinguishable from their cyclized cyclopropane containing counterparts in cell growth inhibition assays, DNA alkylation studies, and in vivo antitumor models.

Due to this indistinguishable behavior, protection of the phenol provides an especially effective site on which to prepare inactive pro-drugs that can be cleaved in vivo releasing the active drug. [For Carzelesin, see: (a) Li et al., Cancer Res. 1992, 52:4904-4913; (b) van Tellingen et al., Cancer Res. 1998, 58:2410-2416; For KW-2189, see: (c) Kobayashi et al., Cancer Res. 1994, 54:2404-2410; (d) Nagamura et al., Chem. Pharm. Bull. 1995, 43:1530-1535; For other CBI carbamate pro-drugs: (e) Boger et al., Synthesis 1999, 1505-1509; (f) Wang et al., Bioorg. Med. Chem. 2006, 14:7854-7861; (g) Li et al., Tetrahedron Lett. 2009, 50:2932-2935; and (h) Wolfe et al., J. Med. Chem. 2012, 55:5878-5886.] Pro-drugs that use this protection and release strategy have been developed where the phenol release in vivo is coupled to features that might permit selective tumor cell delivery or cleavage, but surprisingly few pro-drug classes have been studied to date. [For glycosidic pro-drugs: (a) Tietze et al., Bioorg. Med. Chem. 2001, 9:1929-1939; (b) Tietze et al., Angew. Chem. Int. Ed. 2006, 45:6574-6577; and (c) Tietze et al., Bioorg. Med. Chem. 2008, 16:6312-6318. For reductively activated pro-drugs: (a) Hay et al., J. Med. Chem. 2003, 46:5533-5545; (b) Hay et al., Bioorg. Med. Chem. Lett. 1999, 9:2237-2242; (c) Tercel et al., Angew. Chem. Int. Ed. 2011, 50:2606-2609; (d) Townes et al., Med. Chem. Res. 2002, 11:248-253; and (e) Boger et al., J. Org. Chem. 1999, 64:8350-8362. For other pro-drugs, see: (a) Zhao et al., J. Med. Chem. 2012, 55:766-782; and (b) Pors et al., K.; Chem. Commun. 2011, 47:12062-12064.]

There are largely two main pro-drug strategies that have been examined for the duocarmycins. The most widely examined strategy utilizes an acylation of the phenol that can be cleaved hydrolytically or enzymatically. Many groups have examined such ester and carbamate pro-drugs [for Carzelesin, see: (a) Li et al., Cancer Res. 1992, 52:4904-4913; (b) van Tellingen et al., Cancer Res. 1998, 58:2410-2416; For KW-2189, see: (c) Kobayashi et al., Cancer Res. 1994, 54:2404-2410; (d) Nagamura et al., Chem. Pharm. Bull. 1995, 43:1530-1535; For other CBI carbamate pro-drugs: (e) Boger et al., Synthesis 1999, 1505-1509; (f) Wang et al., Bioorg. Med. Chem. 2006, 14:7854-7861; (g) Li et al., Tetrahedron Lett. 2009, 50:2932-2935; and (h) Wolfe et al., J. Med. Chem. 2012, 55:5878-5886] and two such derivatives, KW-2189 [Kobayashi et al., Cancer Res. 1994, 54:2404-2410] and carzelesin [Li et al., Cancer Res. 1992, 52:4904-4913], entered clinical trials. With the exception of a notable recent example [Wang et al., Bioorg. Med. Chem. 2006, 14:7854-7861], these have been traditionally designed to permit rapid free drug release upon in vivo administration and typically incorporate functionality to improve the drug physical properties (e.g., solubility).

The second but less extensively explored approach involves the development of functionality that can be reductively activated. [Wolkenberg et al., Chem. Rev. 2002, 102:2477-2495.] Past examples include Denny's nitro precursors to aryl amine variants of the phenol drugs [Hay et al., J. Med. Chem. 2003, 46:5533-5545], Lee's use of an ester that is subject to cleavage upon a tethered quinone reduction [Townes et al., Med. Chem. Res. 2002, 11:248-253], and a report of mitomycin-like quinone precursors that undergo an analogous o-spirocyclization upon reductive activation by the inventor and co-workers [Boger et al., J. Org. Chem. 1999, 64:8350-8362].

More recently, the inventor and co-workers introduced a set of N-acyl O-amino phenol pro-drugs that were designed to potentially take advantage of the hypoxic tumor environment and its increased concentration of reducing nucleophiles such as glutathione that can cleave an activated N—O bond (below) [Jin et al., J. Am. Chem. Soc. 2007,

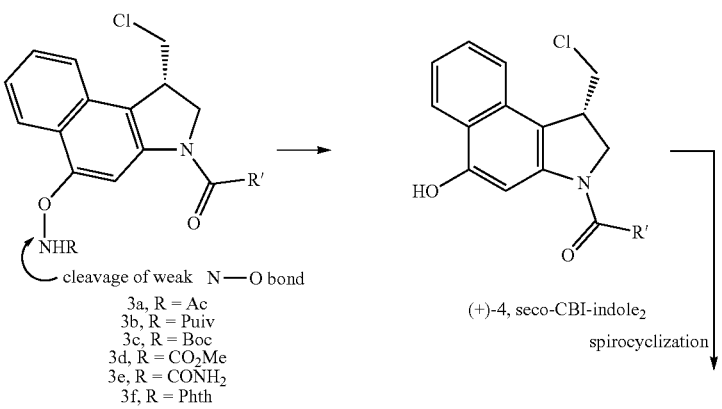

cleavage of weak N—O bond

3a, R = Ac
3b, R = Puiv
3c, R = Boc
3d, R = CO₂Me
3e, R = CONH₂
3f, R = Phth (+)-4, seco-CBI-indole₂ spirocyclization

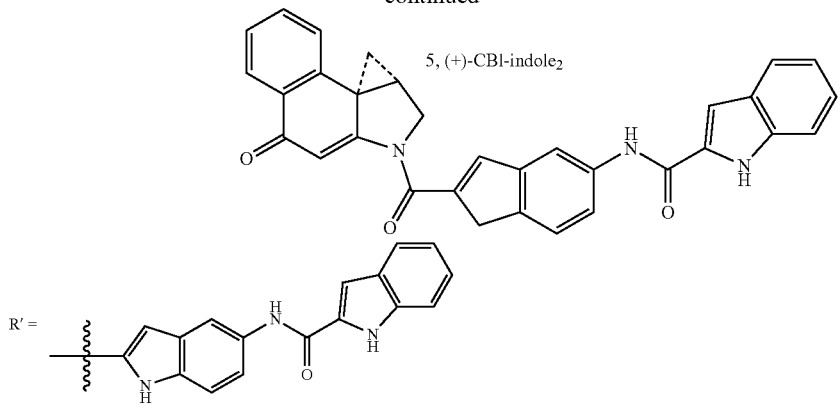

129:15391-15397 and U.S. Pat. No. 8,377,981; and (b) Lajiness et al., *J. Med. Chem.* 2010, 53:7731-7738]. Just as significantly, intracellular concentrations of such reducing thiols are as much as 100-fold higher than plasma concentrations, suggesting that, unlike the more traditional carbamates, such reductively-activated pro-drugs can be subject to preferential intracellular release. Precedent for the behavior of such pro-drugs can be found in the natural product FR900482 and its related congeners [(a) Paz et al., *J. Am. Chem. Soc.* 1997, 119:5999-6005; and (b) Williams et al., *Chem. Biol.* 1997, 4:127-137; and Tepe et al., *Tetrahedron* 2002, 58:3553-3559] that contain hydroxylamine hemiketals and are irreversibly activated by reductive cleavage of an N—O bond.

In initial studies by the inventor and co-workers, a remarkable range of pro-drug stability and propensity for N—O bond cleavage was observed even with subtle variations in the electronic and steric environment around the weak N—O bond. Significantly, the in vivo evaluation of several such pro-drugs demonstrated that those that exhibit a balanced N—O stability/reactivity approach the potency and substantially exceed the efficacy of the free drug itself, suggesting that such pro-drugs can afford advantages related to their controlled or targeted release.

BRIEF SUMMARY OF THE INVENTION

Based on the above-discussed demonstrated capability to structurally tune the free drug release using reductive activation, a unique cyclic variant of the N-acyl O-amino phenol motif has been examined and found particularly useful. Herein, the synthesis and biological evaluation of two specific cyclic oxazinone N—O CBI-pro-drugs (Compounds +6 and +7), below, that can be reductively cleaved to provide the

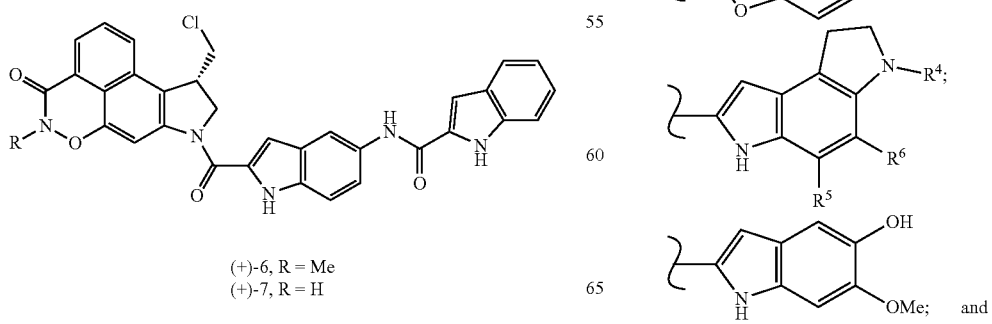

active compound without the accompanying release of any extraneous material are used as illustrative examples of the genus of compounds contemplated.

More generally, a contemplated compound can be depicted by Formula I, below

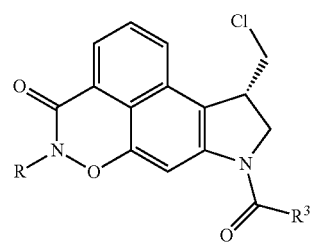

where R is hydrido (H), or $C_1$-$C_6$ hydrocarbyl and $R^3$ is selected from group consisting of radicals represented as follows:

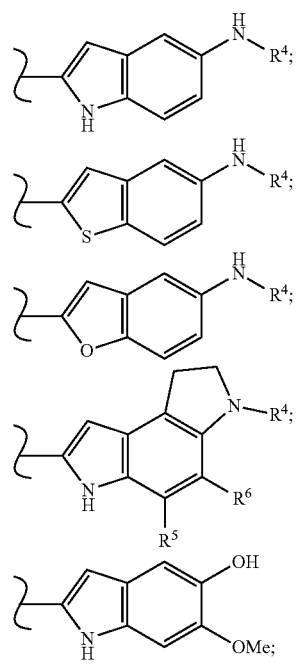

-continued

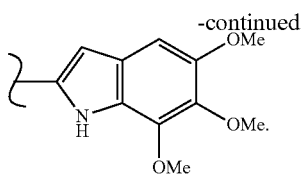

wherein R⁴ is selected from group consisting of radicals represented as follows:

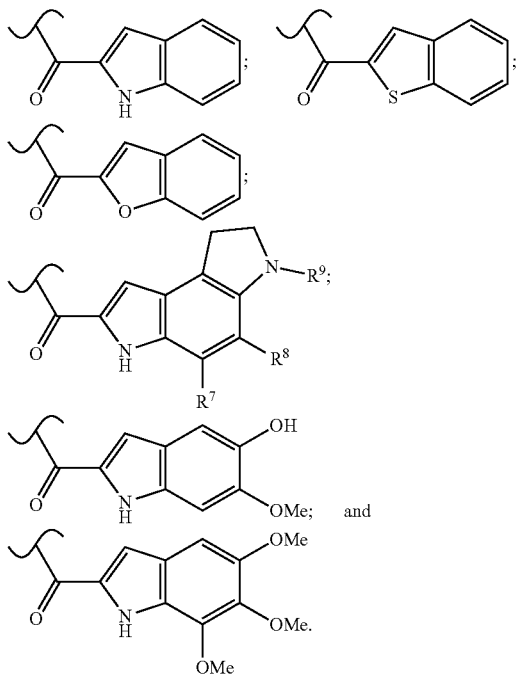

and $R^5$, $R^6$, $R^7$ and $R^8$ in the above structural formulas are each independently selected from the group of radicals consisting of —H, —OH, —O($C_1$-$C_6$ hydrocarbyl), —($C_1$-$C_6$ hydrocarbyl) and halogen. $R^9$ of an above formula is selected from the group of radicals consisting of —H, —C(O)O($C_1$-$C_6$ alkyl), —C(O)($C_1$-$C_6$ hydrocarbyl), —C(O)NH$_2$, —C(O)NHNH$_2$, and —C(O)NHNHC(O)O($C_1$-$C_6$ hydrocarbyl).

A process for treating a proliferative disease such as a cancer or leukemia in a mammal is also contemplated. In accordance with that process, an effective amount of a compound of Formula I such as one of the two compounds shown immediately above is administered to a mammal in need thereof. In yet another aspect, the use of a compound of Formula I in the manufacture of a medicament for treating a proliferative disease such as cancer or leukemia is contemplated.

It is noted that in the structural formulas utilized herein that a wavy line indicates a chemical bond of undefined stereochemistry to a depicted atom. It is also noted that to improve readability and minimize seeming duplication, any combination of structural elements described broadly can be present in a specific embodiment unless otherwise stated.

BRIEF DESCRIPTION OF THE DRAWINGS

In the drawings forming a portion of this disclosure.

DEFINITIONS

Figure 1:
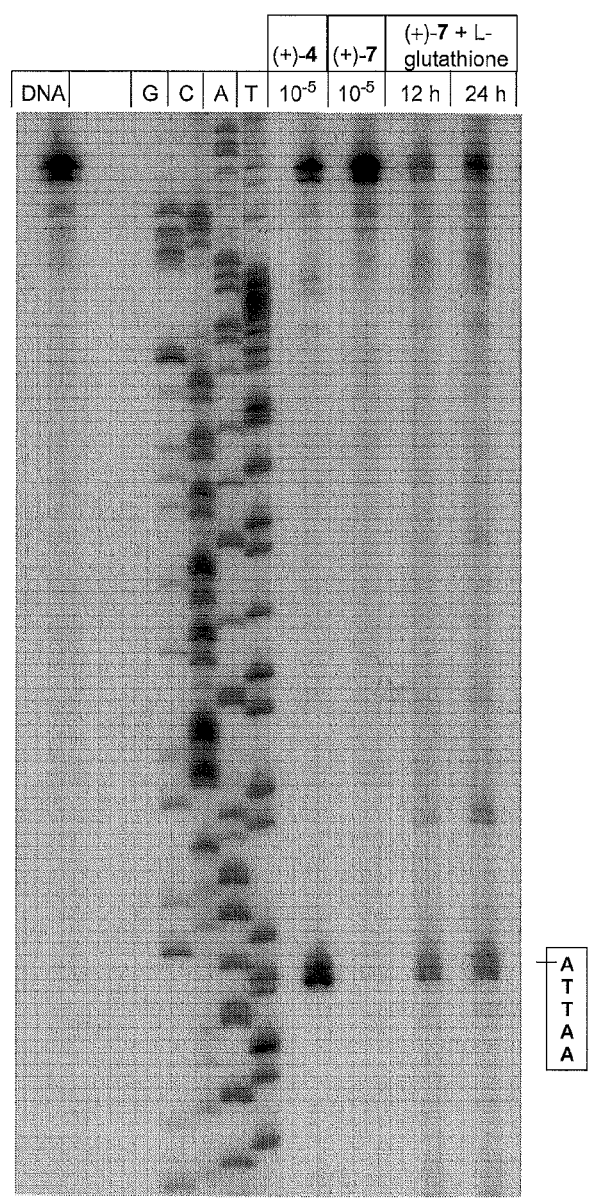
FIG. 1 is a photograph of a DNA sequencing polyacrylamide gel autoradiograph in which DNA alkylation by Compound (+)-7 in w794 DNA is illustrated. No DNA alkylation by Compound (+)-7 is observed in the absence of activation (lane 7), whereas thiol addition (L-glutathione) releases the free drug and results in DNA alkylation (lanes 8 and 9) at sites observed with (+)-CBI-indole$_2$ (lane 6). DNA-agent incubation at 23° C. for 2 hours (h), removal of unbound agent by EtOH precipitation, and 30 minute thermolysis (100° C.) followed by 8% denaturing PAGE and autoradiography. Lane 1, control DNA; lanes 2-5, Sanger G, C, A, and T sequencing reactions; lane 6, Compound (+)-4 (1×10⁻⁵ M); lane 7, Compound (+)-7 (1×10⁻⁵ M); lanes 8-9, Compound (+)-7 (1×10⁻⁵ M) incubated at 37° C. with 1 M L-glutathione for 12 hours and 24 hours. This DNA alkylation behavior of Compound (+)-7 proved to be analogous to that of Compound (+)-3c (FIG. 2) that also fails to effectively alkylate DNA in the cell free assay, but does so effectively upon activation by addition of L-glutathione.
Figure 2:
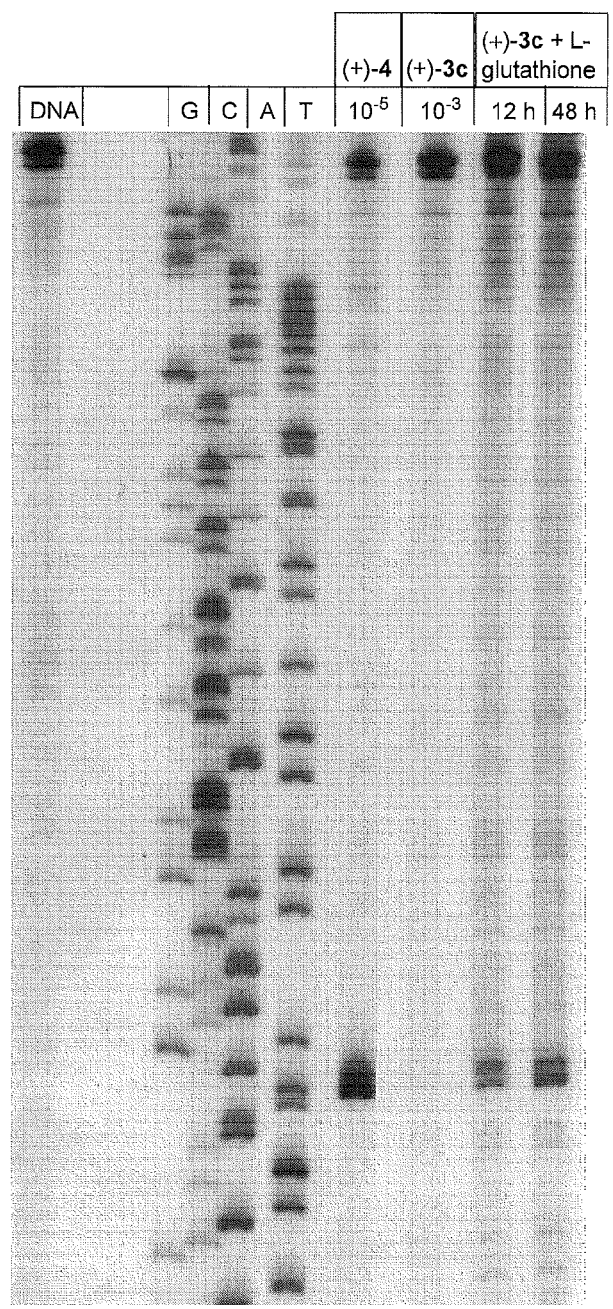
FIG. 2 is a DNA sequencing polyacrylamide gel autoradiograph in which DNA alkylation by Compound 3c in w794 DNA. No DNA alkylation by Compound (+)-3c is observed in the absence of activation (lane 7), whereas thiol addition (L-glutathione) releases the free drug and results in DNA alkylation (lanes 8 and 9) at sites observed with (+)-CBI-indole$_2$ (lane 6). DNA-agent incubation at 23° C. for 2 hours (h), removal of unbound agent by EtOH precipitation, and 30 minutes thermolysis (100° C.) followed by 8% denaturing PAGE and autoradiography. Lane 1, control DNA; lanes 2-5, Sanger G, C, A, and T sequencing reactions; lane 6, Compound (+)-4 (1×10⁻⁵ M); lane 7, Compound (+)-3c (1×10⁻³ M); lanes 8-9, Compound (+)-3c (1×10⁻⁵ M) incubated at 37° C. with 1 M L-glutathione for 12 hours and 48 hours.

In the context of the present invention and the associated claims, the following terms have the following meanings:
The articles "a" and "an" are used herein to refer to one or to more than one (i.e., to at least one) of the grammatical object of the article. By way of example, "an element" means one element or more than one element.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_6$ alkyl, methyl or tert-butyl. Exemplary hydrocarbyl groups contain a chain of 1 to 4 carbon atoms, and preferably 1 or 2 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl. Examples of suitable alkenyl radicals include ethenyl (vinyl), 2-propenyl, 3-propenyl, 1,4-butadienyl, 1-butenyl, 2-butenyl, and 3-butenyl. Examples of alkynyl radicals include ethynyl, 2-propynyl, 1-propynyl, 1-butynyl, 2-butynyl, 3-butynyl, and 1-methyl-2-propynyl.

As a skilled worker will understand, a substituent that cannot exist such as a $C_1$ alkenyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, and tert-butoxy groups.

The term "ring structure" is used herein to mean a cyclic substituent that can contain a single ring such as an imidazolyl or phenyl group, or two fused rings as are present in a naphthyl, purinyl, indolyl, or decalinyl group, or two linked rings as are present in a biphenyl group.

The term "cyclohydrocarbyl" or "carbocyclic", alone or in combination, means a cyclic hydrocarbyl radical (or ring) that contains 5 to about 12 carbon atoms, preferably about 5 to about 10 carbon atoms. Examples of such cyclohydrocarbyl radicals include cyclopropyl, cyclobutyl, cyclopentenyl, cyclohexyl, cycloheptynyl, 1- and 2-decalinyl and the like.

The term "aryl", alone or in combination, means an aromatic ring system. Such a ring system includes a phenyl, naphthyl and biphenyl ring system.

The heterocyclyl (heterocyclo) is a single 5- or 6-membered ring or a fused or linked 5,5-5,6-6,6-ring system that contains 1 to 4 hetero atoms (non-carbons) in the ring that independently are nitrogen, oxygen or sulfur atoms in a saturated or partially unsaturated ring. Examples of such heterocyclyl groups are pyrrolidinyl, piperidinyl, piperazinyl, morpholinyl, thiamorpholinyl, oxathiazolyl, 1,2,3-triazolyl, 1,2,4-triazolyl, pyrazolyl, 1,2,4-oxadiazinyl and azepinyl groups and a bipiperidinyl group.

A "heteroaryl" group is an aromatic heterocyclic ring that preferably contains one, or two, or three or four atoms in the ring other than carbon. Those heteroatoms can independently be nitrogen, sulfur or oxygen. A heteroaryl group can contain a single 5- or 6-membered ring or a fused ring system having two 6-membered rings or a 5- and a 6-membered ring, or a linked 5,5-, 5,6- or 6,6-membered rings as in a bipyridinyl group. Exemplary additional heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

DETAILED DESCRIPTION OF THE INVENTION

A novel genus of cyclic N-acyl O-amino reductively activated phenol pro-drugs related to the duocarmycin class of compounds and their use are disclosed. These compounds do not require enzymatic release and are illustrative of other phenolic drugs that can benefit from such a designed activation.

A contemplated compound can be depicted by Formula I, below, where R is hydrido (H), or $C_1$-$C_6$

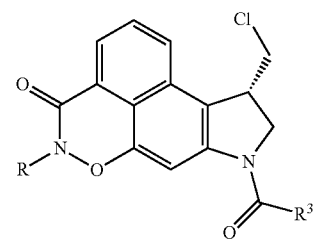

hydrocarbyl and $R^3$ is selected from group consisting of radicals represented as follows:

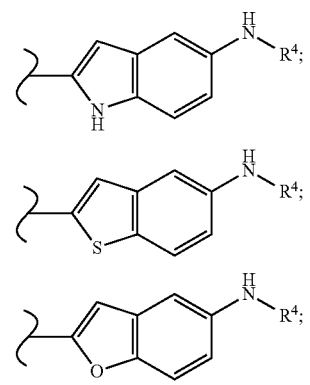

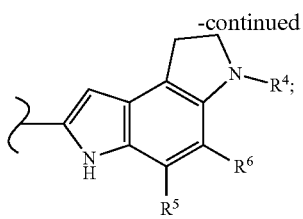

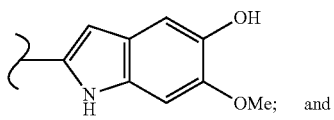

wherein R⁴ is selected from group consisting of radicals represented as follows:

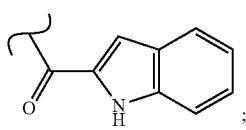

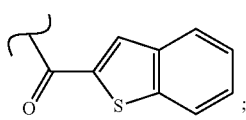

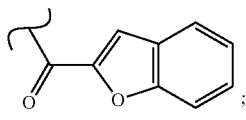

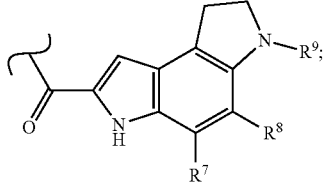

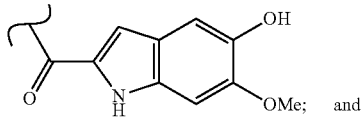

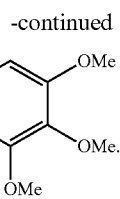

$R^5$, $R^6$, $R^7$ and $R^8$ in the above structural formulas are each independently selected from the group of radicals consisting of —H, —OH, —O($C_1$-$C_6$ hydrocarbyl), —($C_1$-$C_5$ hydrocarbyl) and halogen. $R^9$ of an above formula is selected from the group of radicals consisting of —H, —C(O)O($C_1$-$C_6$ alkyl), —C(O)($C_1$-$C_6$ hydrocarbyl), —C(O)NH$_2$, —C(O)NHNH$_2$, and —C(O)NHNHC(O)O($C_1$-$C_6$ hydrocarbyl).

Hydrido (H) and methyl ($C_1$ hydrocarbyl) are preferred R groups. Preferred $R^3$ groups are

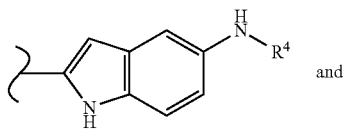

and

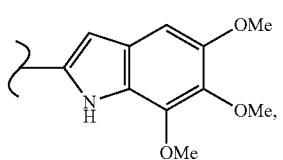

whereas preferred $R^4$ substituents are

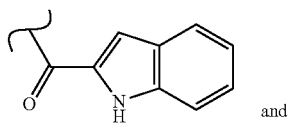

and

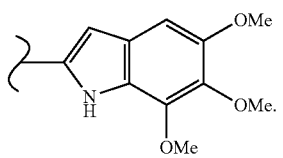

Illustrative preferred compounds of Formula I include those whose structural formulas are shown below, wherein R is preferably hydrido or methyl and the other R groups are as defined above.

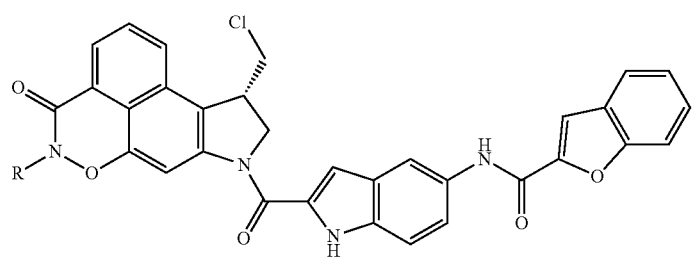

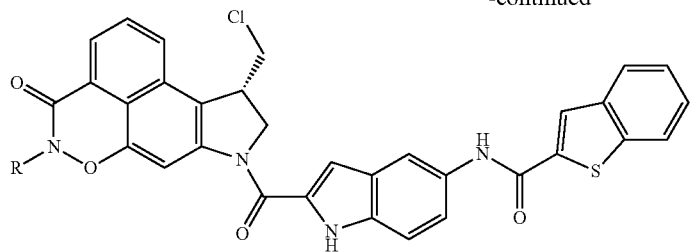
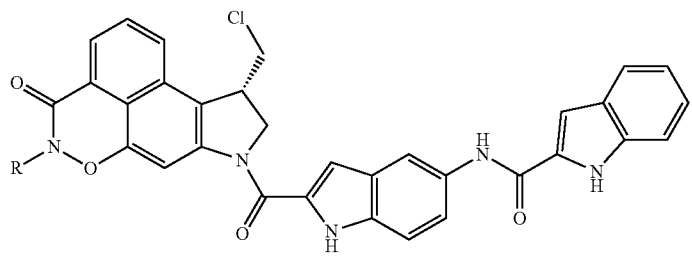
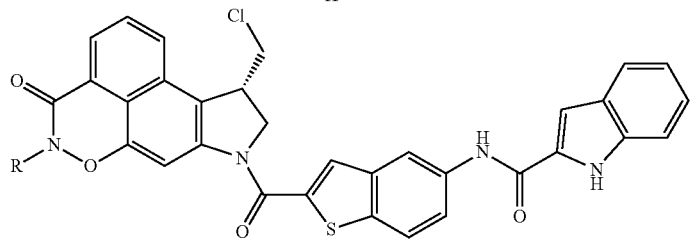
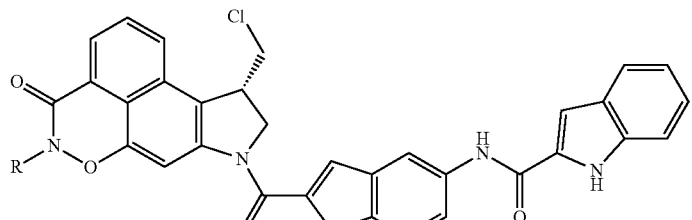
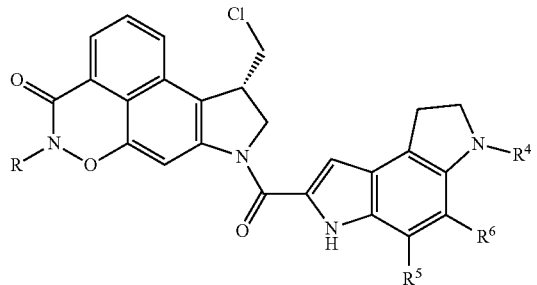
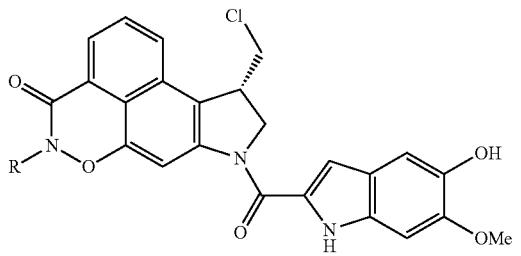
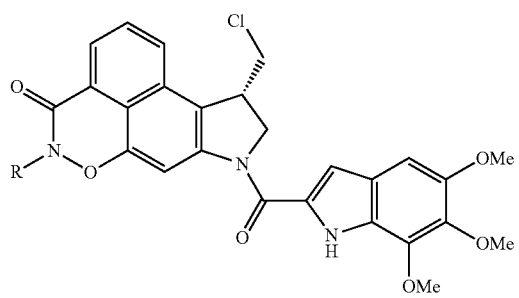

-continued
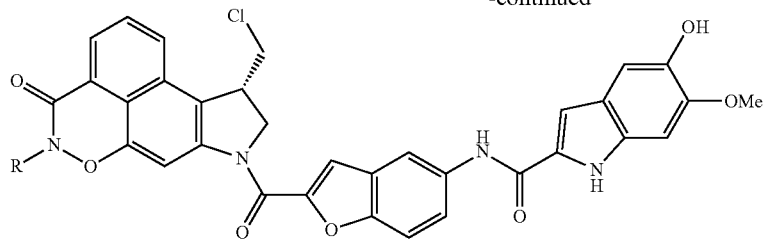
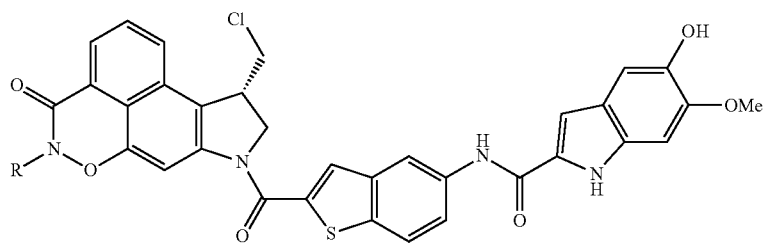
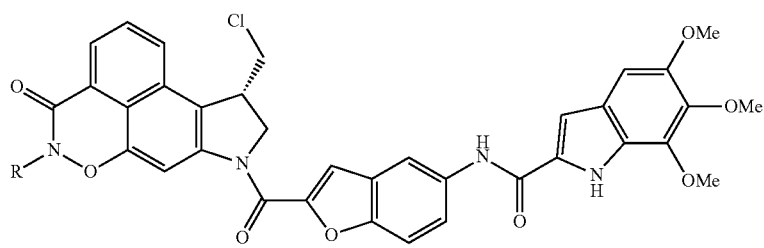
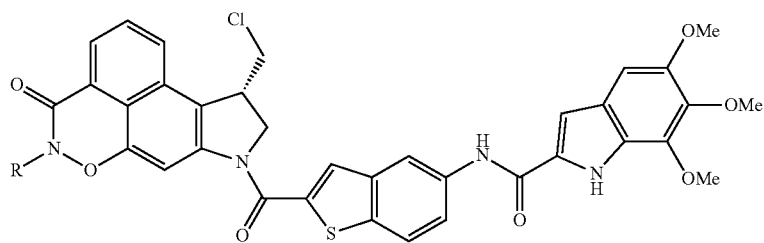
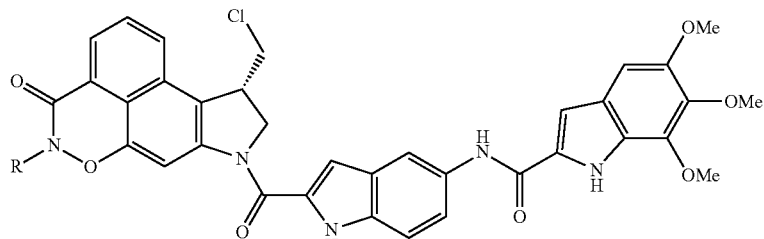
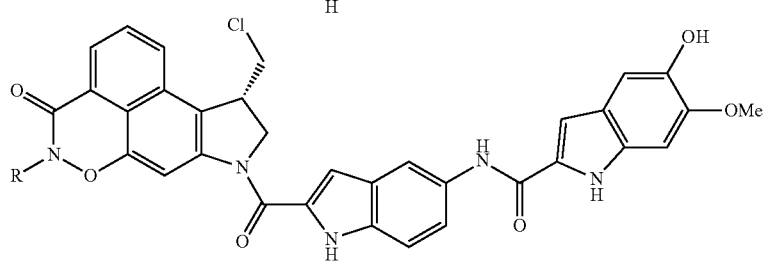

Compounds (+)6 and +(7), below, are particularly preferred.

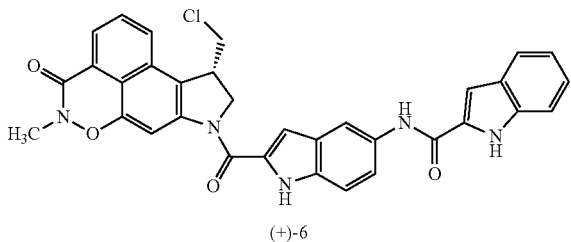

(+)-6

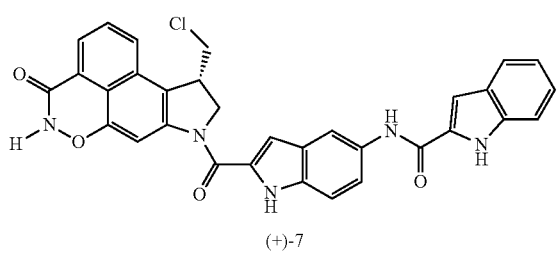

(+)-7

Pharmaceutical Compositions and Treatment Methods

A pharmaceutical composition for treating a proliferative disease such as a cancer or leukemia in a mammal is also contemplated. Such a composition contains a pharmaceutically effective amount (a proliferative disease inhibiting amount) of a before-discussed molecule of Formula I dissolved or dispersed in a pharmaceutically acceptable diluent.

A contemplated compound of Formula I can be used in a pharmaceutical composition to treat and preferably kill cancer cells or cells of another proliferative disease such as leukemia in vitro or in vivo in a mammalian subject. Thus, an above composition is contacted with the cells to be treated. The cells so treated are maintained in contact with a compound of Formula I until cleared by the body when in vivo, or for various times as desired in an in vitro study. The treatment is generally repeated several times.

A mammal to which or whom a composition containing a compound of Formula I is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like in need of treatment for a cancerous condition.

A contemplated composition is administered to a mammal in need of the medication at an proliferative effective dosage level. That level is typically an amount sufficient to provide about 100 to about 3000 μg/kg of body weight to the recipient's plasma or serum, using the molecular weight of the scission-activated duocarmycin-type pro-drug Compound (+)6 itself as the basis for calculation in view of

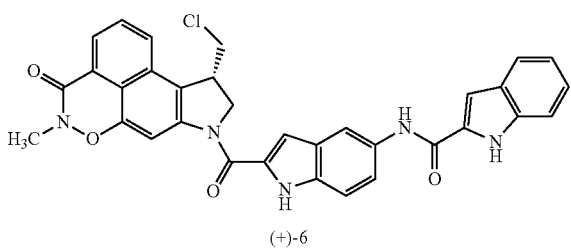 [SMILES: CN1Oc2cc3c(c4cccc(c24)C1=O)[C@H](CCl)CN3C(=O)c1cc2cc(NC(=O)c3cc4ccccc4[nH]3)ccc2[nH]1]

(+)-6 the different molecular weights of the other pro-drug compounds contemplated herein. The amount can vary depending on the recipient and proliferative cell load. The determination of optimum dosages for a particular situation is within the skill of the art.

In an in vitro study using murine leukemia cells, $IC_{50}$ of about 1 nM and about 0.3 nM were found for Compounds (+)6 and (+)7, respectively. An in vivo study comparing Compounds (+)4 and (+)6, a uniquely broad therapeutic window was noted for Compound (+)6 compared to Compound (+)4, in that dosing of Compound (+)4 at 60 to 500 μg/kg, provided premature death to the test mice, whereas administration of Compound (+)6 at 2500 μg/kg provided 6/10 survivors at the one year time period, and 4/10 at each of the two next lower dosages (1000 μg/kg and 500 μg/kg at that time. Data hereinafter.

A composition containing a compound of Formula I is administered repeatedly, on a schedule adapted for a recipient's cancer load and need, as is well known in the art. Typical administrations are given im, iv or ip multiple times within a one month time period, usually followed by a rest period and then further administrations and rest periods until the recipient is free of the disease, or longer for prophylactic purposes.

For preparing pharmaceutical compositions containing a compound of the invention, an inert, pharmaceutically acceptable carrier or diluent is used. The diluent is usually in liquid form.

Liquid pharmaceutical compositions include, for example, solutions suitable for intraparenteral (ip), intramuscular (im) or intravenous (iv) administration. Sterile water solutions of the active or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

Results

Solvolysis of Compound 20

Compound 20 was dissolved in $CH_3OH$ (1.5 mL). The $CH_3OH$ solution was mixed with aqueous buffer (pH 2, 1.5 mL). The buffer contained 4:1:20 (v:v:v) 1.0 M citric acid, 0.2 M $Na_2HPO_4$, and $H_2O$, respectively. After mixing, the solvolysis solutions were stoppered and kept at 25° C. in the dark.

The UV spectrum of the solutions was measured 3-4 times in the first two days and once a day for 2-4 weeks. The UV monitoring was continued until no further change was detectable. The long-wavelength absorption at 380 nm and short-wavelength absorption at 255 nm were monitored. The solvolysis rate constant and half-life were calculated from the data recorded at the short wavelength (255 nm) from the least square treatment of the slopes of plots of time versus ln $[((A_{Final}-A_{Initial})/(A_{Final}-A)]$.

pH 2 buffer: 1.0 M citric acid: 0.2 M $Na_2HPO_4$: $H_2O$ (4:1:20)

$t_{1/2}$=27.8 h, k=8.3×10$^{-6}$ s$^{-1}$ pH 3 buffer: 0.1 M citric acid: 0.2 M Na$_2$HPO$_4$: H$_2$O (4:1:20)

$t_{1/2}$=293 h, k=6.6×10$^{-7}$ s$^{-1}$

Stability and Reactivity of the N—O Pro-Drugs

Because little is known about the chemical reactivity of such oxazinones, the stability of each Boc-protected pro-drug (Compounds 12 and 15), below,

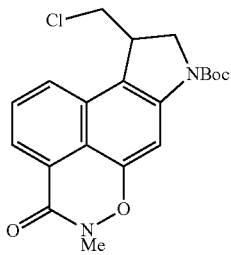

14

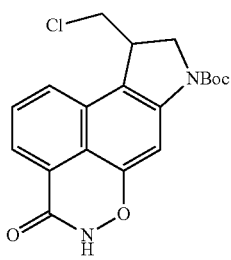

15 and their propensity to release the free drug were examined under representative acidic, basic, and based on observations made throughout their synthesis, both Compounds 12 and 15 are remarkably stable, and Compound 15 proved to be more reactive and less stable than Compound 12 under all conditions examined. In acidic media (4 N HCl/EtOAc, 23° C.), Compounds 12 and 15 exhibited half-lives ($t_{1/2}$) of 24 hours and 2 hours, respectively (after initial Boc deprotection).

The full pro-drug Compound 6 was even more stable, exhibiting half-lives of >72 hours and 30 hours in 4 N HCl/EtOAc and 1:1 TFA/CH$_2$Cl$_2$ at 23° C., respectively. Compound 12 was found to be stable upon exposure to basic conditions, being unreactive toward NaHCO$_3$ in a variety of solvents (THF, MeOH, DMF/H$_2$O, 23° C.) for more than 5 days. Comparatively, the unsubstituted oxazinone Compound 15 was stable to NaHCO$_3$ in THF/H$_2$O at 23° C., but was slowly consumed in MeOH under the same conditions ($t_{1/2}$=70 hours).

Both oxazinones were found to be remarkably stable toward model nucleophiles with Compound 15 exhibiting a more rapid cleavage relative to the more stable Compound 12, with thiols reacting much more effectively than amines (Table 1, below). The greater stability of Compound 12 versus Compound 15 toward nucleophilic cleavage of the N—O bond can be attributed to the increased steric hindrance of the tertiary versus secondary nitrogen consistent with prior observations. [Lajiness et al., *J. Med. Chem.* 2010, 53:7731-7738] Finally, even the more stable of the two pro-drugs (Compound 6) was rapidly cleaved under reductive conditions (H$_2$, Pd/C, MeOH, 23° C., 1 hour or Mo(CO)$_6$, MeCN/H$_2$O, reflux, 3 hours).

TABLE 1

| Entry | Solvent | Nucleophile[a] | Base[a] | 2 h[b] | 24 h[b] | 48 h[b] | 72 h[b] |
|---|---|---|---|---|---|---|---|
| 1 | THF[c] | BnSH | NaHCO$_3$ | 28% | 33% | 39% | 46% |
| 2 | MeOH | BnSH | NaHCO$_3$ | 33% | 58% | 75% | 83% |
| 3 | THF[c] | BnNH$_2$ | NaHCO$_3$ | 2% | 3% | 4% | 3% |
| 4 | MeOH | BnNH$_2$ | NaHCO$_3$ | stable | 9% | 15% | 16% |

[a]excess reagents used;
[b]percent of starting material consumed as determined by LCMS absorption at 254 nM at various times in hours (h);
[c]stable under non-basic conditions The stability of the pro-drug Compound 6 was examined in pH 7.0 phosphate buffer ($t_{1/2}$>4 weeks), human plasma ($t_{1/2}$>1 week, <5% free drug), and mouse plasma ($t_{1/2}$>48 hours), demonstrating that its N—O bond is remarkably stable under such conditions. In contrast, the more reactive pro-drug Compound 7 was found to be slowly reactive in pH 7.0 phosphate buffer ($t_{1/2}$=1 week), and slowly cleaved in human plasma ($t_{1/2}$=4 days) or mouse plasma ($t_{1/2}$>48 hours, <5% free drug).

Biological Properties

DNA Alkylation Properties

Figure 3:
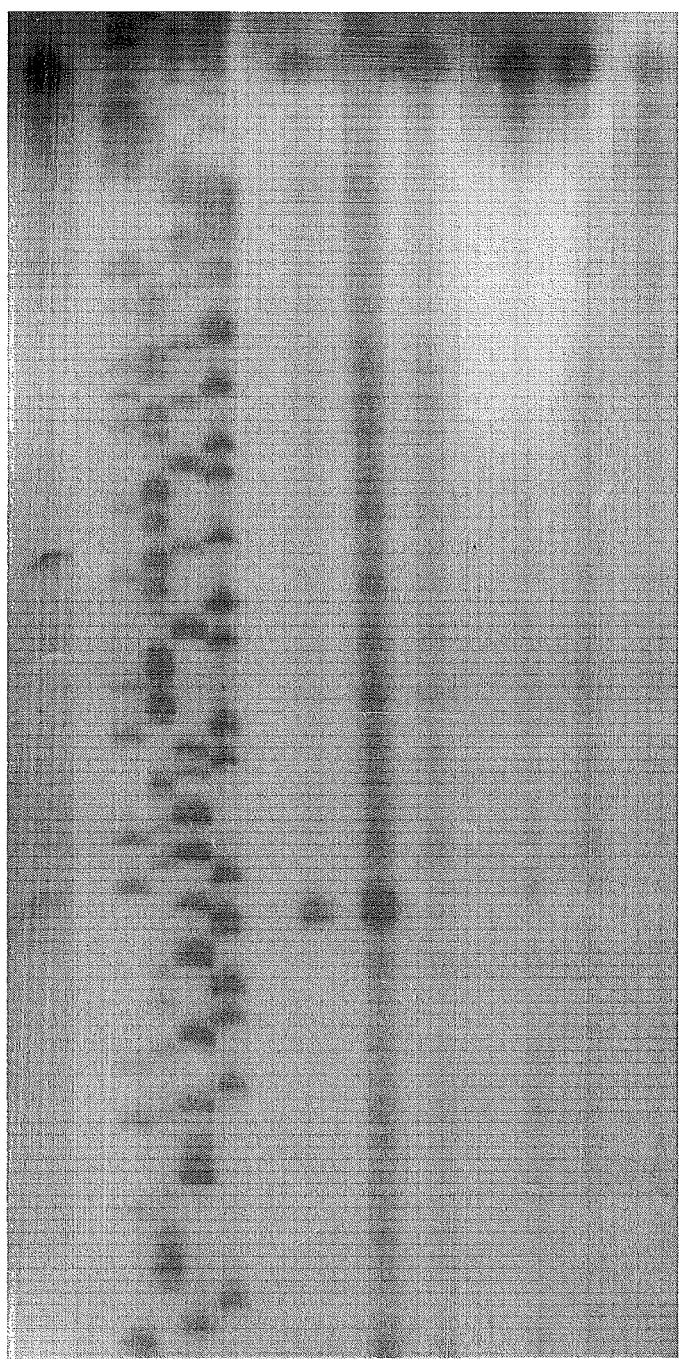
FIG. 3 is a DNA sequencing polyacrylamide gel autoradiograph of thermally-induced strand cleavage of w794 DNA; DNA-agent incubation at 23° C. for 48 hours, removal of unbound agent by EtOH precipitation, and 30 minutes thermolysis (100° C.) followed by 8% denaturing PAGE and autoradiography. Lane 1, control DNA; lanes 2-5, Sanger G, C, A, and T sequencing reactions; lanes 6-8, Compound (+)-4 (1×10⁻⁴ to 1×10⁻⁶ M); lanes 9-11, Compound (+)-6 (1×10⁻² to 1×10⁻⁴ M).
Figure 4:
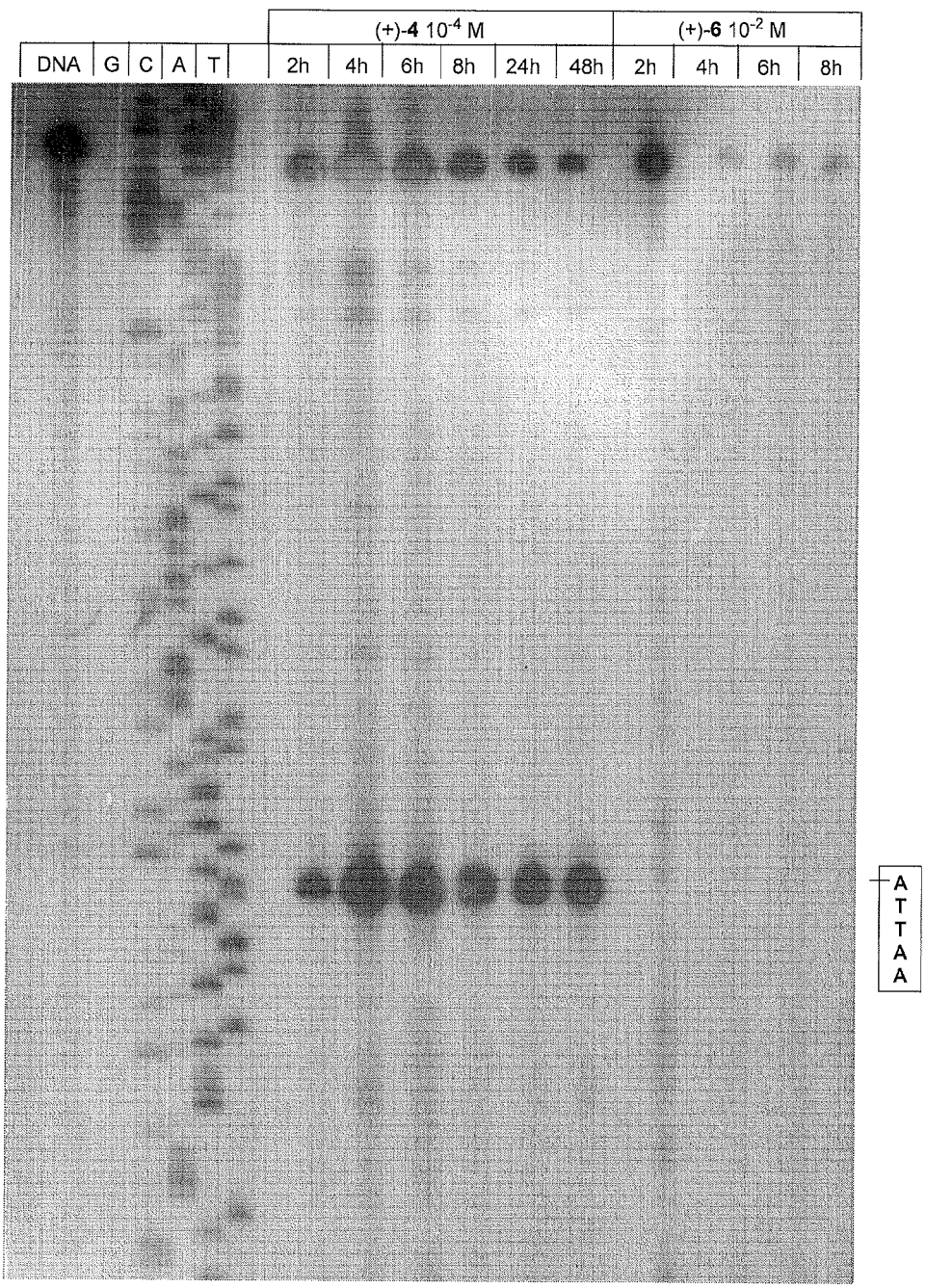
FIG. 4 is a DNA sequencing polyacrylamide gel autoradiograph of thermally-induced strand cleavage of w794 DNA; DNA-agent incubation at 23° C. for t hours, removal of unbound agent by EtOH precipitation, and 30 minute thermolysis (100° C.) followed by 8% denaturing PAGE and autoradiography. Lane 1, control DNA; lanes 2-5, Sanger G, C, A, and T sequencing reactions; lanes 6-11, Compound (+)-4 (1×10⁻⁴M, t=2, 4, 6, 8, 24, 48 hours); lanes 12-15, Compound (+)-6 (1×10⁻²M, t=2, 4, 6, 8 hours).

Consistent with expectations and in the absence of a source of reductive activation, the pro-drug Compound (+)-6 was found to be incapable of alkylating DNA in cell-free systems [(a) Boger et al., *Tetrahedron* 1991, 47:2661-2682; and (b) Boger et al., *J. Am. Chem. Soc.* 2001, 123:5878-5891] at concentrations as much as 1000-fold higher than those where the free drug Compound (+)-4 are effective (FIGS. 3 and 4). Similarly, the pro-drug Compound (+)-7 failed to alkylate DNA in a cell free assay without deliberate activation, whereas addition of L-glutathione promoted an effective, time-dependent release of the free drug and a slow DNA alkylation reaction that proceeded with a selectivity identical to that of the parent free drug (FIG. 1).

Free drug Compound 19, below, released upon

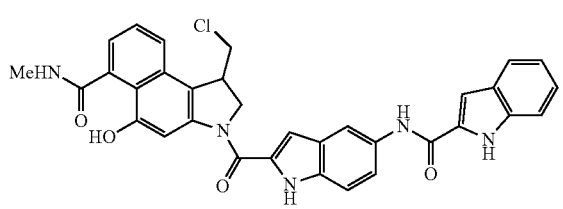

Figure 5:
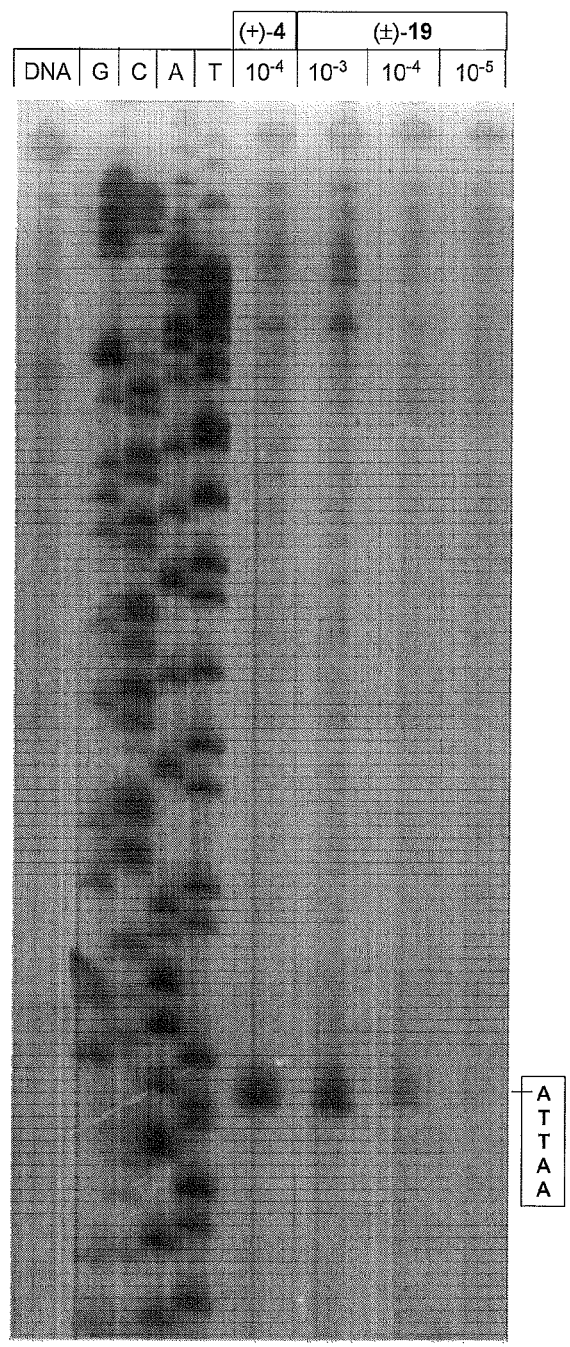
FIG. 5 is a DNA sequencing polyacrylamide gel autoradiograph of thermally-induced strand cleavage of w794 DNA; DNA-agent incubation at 23° C. for 48 hours, removal of unbound agent by EtOH precipitation, and 30 minute thermolysis (100° C.) followed by 8% denaturing PAGE and autoradiography. Lane 1, control DNA; lanes 2-5, Sanger G, C, A, and T sequencing reactions; lane 6, Compound (+)-4 (1×10⁻⁴ M); lanes 7-9, Compound (±)-19 (1×10⁻³ to 1×10⁻⁵ M).

19 reductive cleavage of Compound (+)-6, was found to alkylate DNA in a manner analogous to Compound (+)-4, indicating that the C5-carboxamide does not significantly alter the DNA alkylation properties and capabilities of the parent drug Compound 4 (FIG. 5).

These studies indicate that the in vitro cytotoxic activity and in vivo antitumor activity of the N—O pro-drugs are not likely derived from the pro-drug Compounds 3, 6, or 7 themselves, but are the result of their reductive cleavage to release the free phenols that in turn are effective DNA alkylating agents and potent cytotoxic compounds. Moreover, the studies indicate that thiols alone are capable of providing this reductive activation through nucleophilic cleavage of the N—O bond, although they do not preclude other reductive mechanisms being operative as well.

In Vitro Cytotoxic Activity

Both enantiomers of Compounds 6 and 7 as well as their precursor Compounds 12 and 15 were tested for cell growth inhibition in a cytotoxic assay with L1210 murine leukemia cells alongside the free drug Compound 19 and related control compounds (Table 2, below). Pro-drug Compound (+)-6 was found to exhibit an $IC_{50}$ of 0.99 nM, whereas the more

TABLE 2

| Compound | IC$_{50}$ L1210 | |
|---|---|---|
| | natural (nM) | unnatural (nM) |
| 1, duocarmycin SA | 0.010 | 0.100 |
| 2, CC-1065 | 0.020 | 0.020 |
| 4, seco-CBI-Indole$_2$ | 0.030 | 0.900 |
| 6 | 0.99 | 740 |
| 7 | 0.30 | 65 |
| (±)-19 | 0.073 | |
| (+)-N—Boc-CBI | 80 | 900 |
| 12 | 850 | >1000 |
| 15 | 650 | >1000 | reactive pro-drug Compound (+)-7 was by comparison, found to have an $IC_{50}$ of 0.30 nM. seco-CBI-indole$_2$ derivatives that lack a C5 substituent needed to support a spirocyclization (e.g., H or OMe) exhibit $IC_{50}$ values at least 100-fold higher than Compound (+)-6 and 350-fold higher than Compound (+)-7 ($IC_{50}$>100 nM, L1210). [a] Jin et al., J. Am. Chem. Soc. 2007, 129:15391-15397; and (b) Lajiness et al., J. Med. Chem. 2010, 53:7731-7738.]

The 3-fold difference in potency between Compound (+)-6 and Compound (+)-7 reflects their relative reactivities toward N—O cleavage with the more reactive pro-drug providing a more facile release of the free drug under the conditions on the assay. Both pro-drug unnatural enantiomers, Compounds (−)-6 and (−)-7, were found to be >200 fold less potent than the natural enantiomers. The parent free drug Compound 19, tested as a racemic mixture, was found to be 2.5 times less potent than seco-(+)-CBI-indole$_2$, indicating that its natural enantiomer closely approximates the activity of (+)-CBI-indole$_2$. Combined, these studies indicate that the pro-drugs Compound 6 and Compound 7 are effectively, but not rapidly or completely cleaved to provide the free drug under the conditions of the assay because their $IC_{50}$ values are between 8- and 25-fold higher than the free drug Compound 19 itself.

Despite this lower in vitro potency relative to the free drug, it is notable that both pro-drugs still display sub-nanomolar cellular potency, being more potent than most clinically used antitumor agents. Moreover, their inherent chemical stability suggests that they, like Compound 3c, possess an appropriate balance between chemical stability and reductive cleavage propensity to display more efficacious in vivo antitumor activity than the free drug itself.

In Vivo Antitumor Activity

Although the results of the functional cellular assays show that Compound (+)-6 is less potent than its parent drug Compound 19 and less potent than Compound (+)-7, the slow release of the free drug could prove advantageous in vivo due to the parent compound's remarkable potency and inherent toxicity. [Wolfe et al., J. Med. Chem. 2012, 55:5878-5886.] Therefore, the preliminary evaluation of the in vivo antitumor activity of the cyclic N—O pro-drugs was assessed with Compound (+)-6 and was conducted alongside seco-CBI-indole$_2$ (Compound 4) in an antitumor model consisting of L1210 murine leukemia cells implanted ip in B6D2F1 mice traditionally used to initially compare new duocarmycin derivatives (Table 3, below).

TABLE 3

| Compound | Dose μg/kg[a] | MSP days[b] | T/C[c] | Surviving Mice[d] |
|---|---|---|---|---|
| none | 0 | 17.6 | 100 | 0/10 |
| 4 | 60 | >50 | >284 | 1/10 |
| 4 | 100 | 6.4 | 36 | 0/10 |
| 4 | 250 | 3.7 | 21 | 0/10 |
| 4 | 500 | 3.0 | 17 | 0/10 |
| 6 | 60 | 28 | 159 | 0/10 |
| 6 | 200 | >68 | >386 | 1/10 |
| 6 | 500 | >201 | >1142 | 4/10 |
| 6 | 1000 | >199 | >1130 | 4/10 |
| 6 | 2500 | >264 | >1500 | 6/10 |

[a]Dose (μg/kg wt. of animal) administered i.p. on days 1, 5 and 9.
[b]MSP = Mean Survival Period (days).
[c]T/C = Treated/Control (MSP) × 100.
[d]Number of live animals after 366 days (terminated).

A dose range of 60 to 2500 μg/kg for pro-drug Compound (+)-6 (scaled to its determined $IC_{50}$) and 60 to 500 μg/kg for seco-CBI-indole$_2$ (Compound 4), and a dosing schedule (administered ip three times on days 1, 5, and 9) traditionally used for this class of compounds were employed. A subtle, but important additional empirical observation made in the studies was that the pro-drug administration was tolerated at the injection sites of the animals much better than the free drug.

seco-CBI-indole$_2$ [Compound (+)-4] was administered at a range (60 to 500 μg/kg) beyond its optimal dosing (60 or 100 μg/kg) [(a) Boger et al., Bioorg. Med. Chem. 1995, 3:1429-1453; and (b) Boger et al., Bioorg. Med. Chem. Lett. 1991, 1:115-120; and a) Jin et al., J. Am. Chem. Soc. 2007, 129:15391-15397; and (b) Lajiness et al., J. Med. Chem. 2010, 53:7731-7738] to highlight its small therapeutic window in comparison to the potential efficacy of pro-drug Compound (+)-6. As previously observed, administration of Compound (+)-4 at 60 μg/kg resulted in only 1/10 long term survivor (T/C>284) at the termination of the study (366 days). At all higher doses (100-500 μg/kg), Compound (+)-4 proved toxic leading to premature death of the animals due to drug toxicity.

Remarkably, administration of Compound (+)-6 produced 6/10 long term survivors at 2500 μg/kg (T/C>1500) and 4/10 long term survivors at the next two lower doses of 1000 μg/kg (T/C>1130) and 500 μg/kg (T/C>1142). Because the response to the administration of Compound (+)-6 was so remarkable, the length of the study was extended to 366 days (1 year) where the live animals represent long term survivors with no evidence of a delayed toxicity.

Even at a dose of Compound (+)-6 (200 μg/kg) only 3-fold higher than the optimal dose of Compound (+)-4 (60 μg/kg), the pro-drug outperformed the free drug (T/C 386 vs 284). These data indicate that Compound (+)-6 does not suffer from the characteristic toxicity of Compound (+)-4 even at 40-fold higher doses, that it possesses a much larger therapeutic window (200 to >2500 μg/kg) compared to the narrow 30 to 100 μg/kg dose range of Compound (+)-4 [(a) Boger et al., Bioorg. Med. Chem. 1995, 3:1429-1453; and (b) Boger et al., *Bioorg. Med. Chem. Lett.* 1991, 1:115-120; and a) Jin et al., *J. Am. Chem. Soc.* 2007, 129:15391-15397; and (b) Lajiness et al., *J. Med. Chem.* 2010, 53:7731-7738], and that it is much more and extraordinarily efficacious in vivo.

It is possible that the pro-drug Compound (+)-6 could benefit from an even higher dosing level or alternative dose schedule beyond this initial exploration, and that such higher doses may be even more efficacious. Although these studies do not directly establish that the free drug is released in vivo nor do they define the site or mechanism of free drug release, the studies do suggest that the in vivo behavior of the cyclic N-acyl O-amino phenol pro-drug benefits from either its controlled slow release of the free drug or its targeted intracellular reductive cleavage.

CONCLUSIONS

Two novel cyclic N-acyl O-amino phenol duocarmycin-related pro-drugs, illustrative Compounds (+)-6 and (+)-7, were synthesized and analyzed for their antitumor activity as pro-drugs in vitro and in vivo. The pro-drugs were designed to be subject to reductive activation, perhaps being capable of selective cleavage with release of the free drug within an hypoxic tumor cell environment due to the increased presence in such cells of reducing nucleophiles that can cleave the weak N—O bond.

Of the two candidate pro-drugs, N-methyl oxazinone Compound (+)-6 proved more stable than Compound (+)-7, but both proved remarkably stable toward acidic and basic conditions as well as reaction with model nucleophiles. Neither pro-drug was found to be effective at alkylating DNA in cell free assays, but like the N—O pro-drug Compound 3c they were found to be activated for DNA alkylation by thiols (L-glutathione). This reactivity toward cleavage of the protective N—O bond was reflected in their in vitro cytotoxic activity with the more stable pro-drug Compound (+)-6 displaying a less potent $IC_{50}$ (0.99 nM) than the more reactive pro-drug Compound (+)-7 ($IC_{50}$=0.30 nM). Pro-drug Compound (+)-6, which was also found to be stable in pH 7.0 phosphate buffer, mouse plasma, and human plasma, was examined in vivo in a leukemia mouse model conducted for an extended duration (366 days) and found to exhibit extraordinary efficacy (T/C>1500, L1210; 6/10 one year survivors) substantially exceeding the efficacy of the free drug. Pro-drug Compound (+)-6 displayed a therapeutic window of efficacy that is much larger than the free drug permitting dosing ≥40-fold over that of the free drug and yet it displayed an in vivo potency that is within 3-fold of that of the free drug. Clearly, the in vivo behavior of Compound (+)-6 benefits from either a controlled release of the active free drug or its intracellular reductive cleavage. These and related aspects of the in vivo behavior of Compound 6 are under investigation.

EXPERIMENTAL SECTION

General

Reagents and solvents were purchased reagent-grade and used without further purification. Pooled human plasma, with sodium citrate as an anticoagulant, was purchased from Innovative Research and stored at −20° C. THF was freshly distilled from sodium benzophenone ketyl. All reactions were performed in oven-dried glassware under an Ar atmosphere. Evaporation and concentration in vacuo was performed at 20° C. TLC was conducted using precoated $SiO_2$ 60 F254 glass plates from EMD with visualization by UV light (254 or 366 nm). Chiral phase HPLC was performed using a Shimadzu HPLC on a semi-preparative Diacel ChiralCel OD column (0.46 cm×25 cm) with a flow rate of 7 mL/min and with UV detection at λ=254 nm. Optical rotations were determined on a Rudolf Research Analytical Autopol III Automatic Polarimeter (λ=589 nm, 25° C.).

NMR ($^1$H or $^{13}$C) were recorded on Bruker DRX-500 and DRX-600 NMP spectrophotometers at 298K. Residual solvent peaks were used as an internal reference. Coupling constants (J) (H,H) are given in Hz. Coupling patterns are designated as singlet (s), doublet (d), triplet (t), quadruplet (q), multiplet (m), or broad singlet (br). IR spectra were recorded on a Thermo Scientific Nicolet 380 FT-IR spectrophotometer and measured neat. High resolution mass spectral data were acquired on an Agilent Technologies high resolution LC/MSD-TOF, and the detected masses are given as m/z with m representing the molecular ion. The purity of each tested compound (>95%) was determined on an Agilent 1100 LC/MS instrument using a ZORBAX SB-C18 column (3.5 mm, 4.6 mm×50 mm, with a flow rate of 0.75 mL/minute and detection at 220 and 254 nm) with a 10-98% acetonitrile/water/0.1% formic acid gradient.

ABBREVIATIONS USED

CBI, 1,2,9,9a-tetrahydrocyclopropa-[c]benz[e]indol-4-one; DPPA, diphenylphosphoryl azide; LiHMDS, lithium bis(trimethylsilyl)amide; THF, tetrahydrofuran; BnSH, benzyl thiol; BnOH, benzyl alcohol; $BnNH_2$, benzylamine; EtOAc, ethyl acetate; DMF, dimethylformamide; MeOH, methanol.

Materials and Methods

Chemistry

Synthesis

Pro-drugs Compounds 6 and 7 were both synthesized from a common intermediate, carboxylic acid Compound 9 (Scheme 1), below. Carboxylic acid

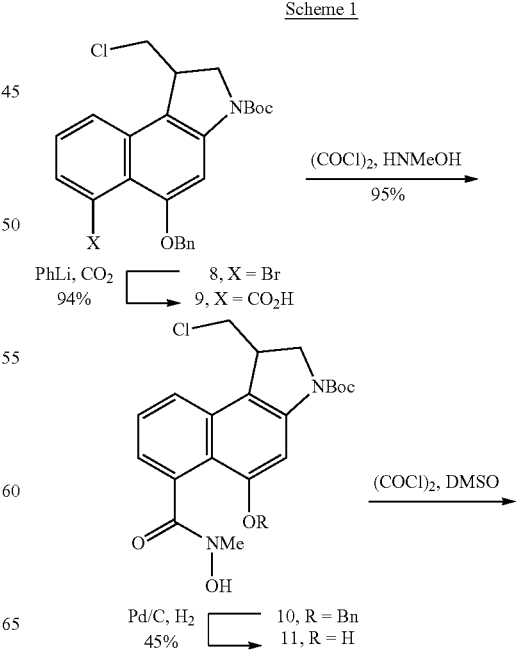

Scheme 1

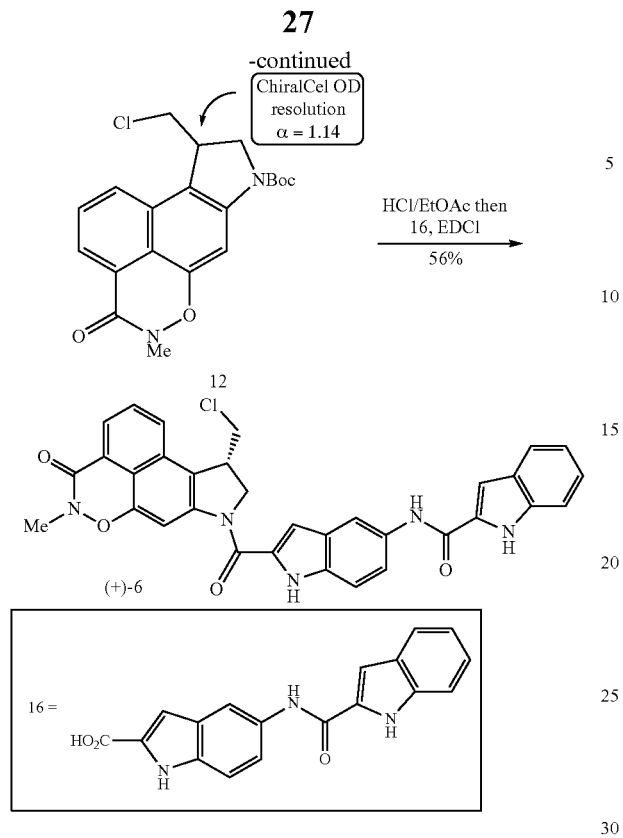

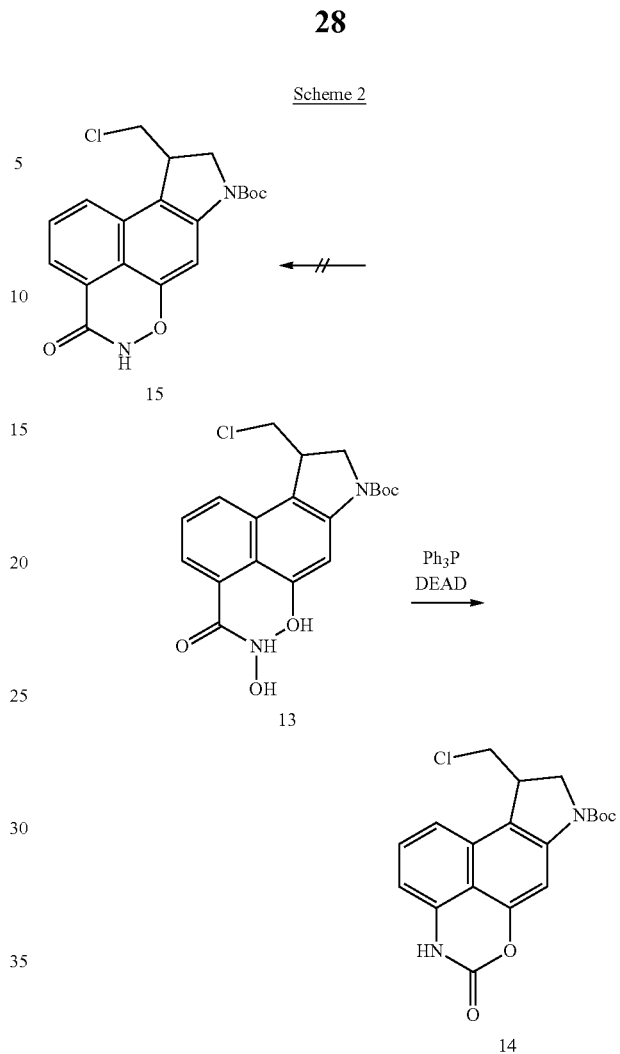

Compound 9 was prepared by phenyl lithium-mediated metal-halogen exchange of the aryl bromide Compound 8 [Wolfe et al., *J. Med. Chem.* 2012, 55:5878-5886] and subsequent trap of the organolithium intermediate with $CO_2$ (g), providing Compound 9 in excellent yield.

The N-methyl oxazinone 11 was produced from Compound 9 in a three-step sequence. First, the acid chloride was formed in situ using oxalyl chloride and catalytic DMF and subsequently condensed with N-methyl hydroxylamine producing the hydroxamic acid Compound 10 in superb yield. The benzyl ether protecting group was removed by palladium-catalyzed hydrogenation, yielding the phenol Compound 11 in a reaction that was run for only 60 minutes to avoid competitive formation of the N—O cleavage byproduct Compound 18 observed at longer reaction times. The key oxazinone was closed upon exposure of Compound 11 to Swern oxidation conditions yielding Compound 12 in modest yield.

This represents a new and unique method for "oxidative" formation of an N—O bond and presumably entails activation of the hydroxamic acid alcohol as its dimethyl sulfoxonium cation for subsequent intramolecular phenol displacement. In contrast and interestingly, attempts to prepare such oxazinones through a Mitsunobu type reaction of the hydroxamic acid Compound 13 using triphenylphosphine ($Ph_3P$) and diethyl azidocarboxylate (DEAD) yielded only the carbamate product Compound 14 produced through a Lossen rearrangement-derived isocyanate (Scheme 2), below.

The racemic N-methyl oxazinone Compound 12 was resolved into its two enantiomers by chiral phase (ChiraCel OD) HPLC with 5% iPrOH/hexanes as the eluent, and each enantiomer was coupled with Compound 16 using EDCI following an acid-catalyzed deprotection of the Boc group providing Compounds (+)- and ent-(−)-6.

The oxazinone Compound 7 bearing a free NH was prepared in an analogous manner with minor changes to the overall synthetic sequence (Scheme 3), below. An activated triazine ester of Compound 9 was

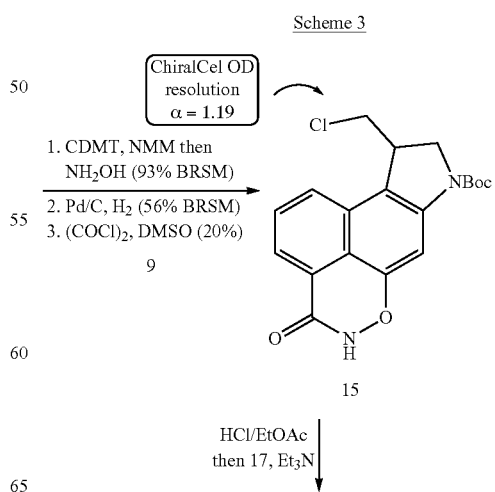

-continued

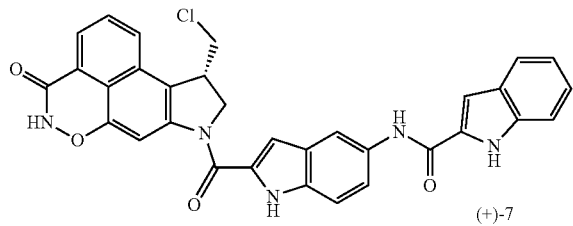

(+)-7

-continued

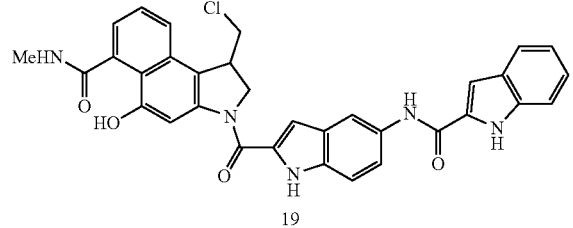

19

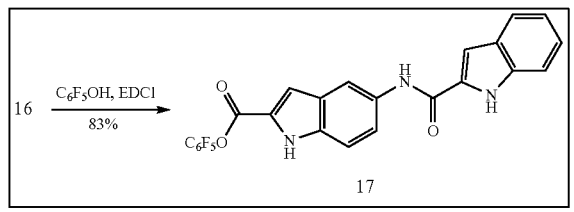

generated upon reaction with 2-chloro-4,6-dimethoxy-1,3,5-triazine (CDMT) and N-methyl morpholine (NMM) and trapped in situ with hydroxylamine to give the corresponding hydroxamic acid. Hydrogenolysis of the benzyl ether to provide Compound 13 and oxazinone closure upon exposure of Compound 13 to Swern oxidation conditions provided Compound 15, but competitive N—O cleavage during the hydrogenation was more facile with the secondary hydroxamic acid and the reaction was more sensitive to the reaction time. Compound 15 was resolved by chiral phase (ChiraCel OD) HPLC with a 15% iPrOH/hexanes eluent.

Boc deprotection of each enantiomer of Compound 15 followed by coupling with Compound 16 using EDCI did not provide Compound 7, presumably due to competitive reaction of the acidic oxazinone. Therefore, the carboxylic acid Compound 16 was first activated as its pentafluorophenyl ester Compound 17 and used in the coupling reaction yielding Compound (+)-7 and ent-(−)-7.

In addition to the key pro-drugs Compounds 6 and 7, the parent N-methyl amide Compound 18 was prepared by extending the hydrogenation time of Compound 10, resulting in removal of the benzyl ether and cleavage of the hydroxamic acid. Acid-catalyzed Boc deprotection of Compound 18 and coupling the released free amine with Compound 16 using EDCI produced the parent free drug Compound 19 as a racemate (Scheme 4) below.

Scheme 4

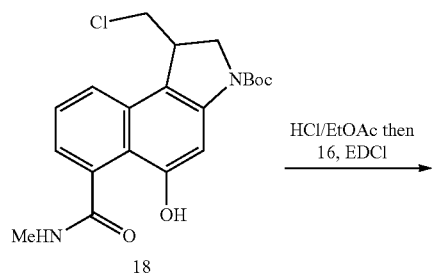

18

HCl/EtOAc then
16, EDCI tert-Butyl 1,2-Dihydro-5-(benzyloxy)-1-(chloromethyl)-6-(carboxylic acid)-benzo[e]indole-3-carboxylate (Compound 9)

Compound 8 (206 mg, 0.409 mmol) was dissolved in freshly distilled anhydrous THF (4.1 mL) and cooled to −78° C. Phenyl lithium (0.23 mL, 2.0 M solution in THF) was added dropwise. After 45 minutes, $CO_2$ (g) was bubbled into the reaction mixture for 10 minutes after which it was allowed to slowly warm to 0° C. The reaction mixture was quenched with the addition 2 N aqueous HCl. The resulting slurry was extracted with $Et_2O$ (3×). The organic extracts were combined, washed with $H_2O$ (2×), saturated aqueous NaCl, dried over $Na_2SO_4$, and concentrated under reduced pressure. Flash chromatography ($SiO_2$, 20-100% EtOAc/hexanes gradient elution) provided Compound 9 (180 mg, 94%) as a tan solid. $^1$H NMR (DMSO-$d_5$, 500 MHz) δ 7.72 (br, 2H), 7.52 (d, J=7 Hz, 1H), 7.38-7.32 (m, 3H), 7.25 (t, J=7.5 Hz, 1H), 6.99 (d, J=7.0 Hz, 1H), 4.11-4.01 (m, 3H), 3.94 (d, J=8.0 Hz, 1H), 3.75 (dd, J=7.5, 11 Hz, 1H) 1.51 (s, 9H). $^{13}$C NMR (DMSO-$d_5$, 150 MHz) δ 154.9, 151.4, 136.7, 136.1, 130.2, 129.1, 128.4, 128.2, 128.1, 127.5, 127.2, 126.7, 125.7, 121.4, 117.1, 114.7, 97.2, 79.8, 69.9, 52.4, 47.6, 27.9. IR (film) $v_{max}$ 2980, 2903, 1693, 1415, 1141 cm$^{-1}$. ESI-TOF HRMS m/z 468.1569 (M+H$^+$, $C_{26}H_{26}ClNO_5$ requires 468.1572).

tert-Butyl 10-(Chloromethyl)-5-methyl-4-oxo-9,10-dihydro-4H-pyrrolo[3',2':5,6]naphtho[1,8-de][1,2]oxazine-8(5H)-carboxylate (Compound 12)

The carboxylic acid Compound 9 (199 mg, 0.420 mmol) in anhydrous $CH_2Cl_2$ (8.5 mL) at 0° C. was treated with (COCl)$_2$ (42 µL, 0.510 mmol). A drop of DMF was added and the reaction mixture was stirred for 1 hour. After 1 hour, a premixed solution of MeNHOH—HCl (177 mg, 2.13 mmol), Et$_3$N (0.29 mL, 2.13 mmol), 3 drops of $H_2O$, and THF (21.3 mL) was added by cannula. After the addition was complete, the reaction mixture was allowed to warm to room temperature over 1 hour. The reaction mixture was concentrated under reduced pressure and then diluted with 2 N aqueous HCl. The aqueous phase was extracted with EtOAc (3×). The organic extracts were combined, washed with $H_2O$ and saturated aqueous NaCl, dried over $Na_2SO_4$, and concentrated under reduced pressure. The crude solid (209 mg, 99%) was carried forward without further purification. ESI-TOF HRMS m/z 497.1854 (M+H$^+$, $C_{27}H_{29}ClN_2O_5$ requires 497.1838).

The N-methyl hydroxamic acid Compound 10 (209 mg, 0.420 mmol) was dissolved in anhydrous $CH_3OH$ (8.4 mL) under Ar. 10% Pd/C (44 mg, 0.0042 mmol) was added and the atmosphere was exchanged with $H_2$. The reaction mixture was allowed to stir at 25° C. for 1 hour. The reaction mixture was diluted with $Et_2O$, filtered through Celite®, and concentrated under reduced pressure. The residue was purified by PTLC (SiO$_2$, EtOAc elution) providing Compound 11 (78 mg, 45%) as an orange foam. ESI-TOF HRMS m/z 407.1367 (M+H$^+$, C$_{20}$H$_{23}$ClN$_2$O$_5$ requires 407.1368).

A stirred solution of (COCl)$_2$ (24 µL, 0.280 mmol) in anhydrous CH$_2$Cl$_2$ (4 mL) at −78° C. was treated with Me$_2$SO (44 µL, 0.570 mmol) in 3 mL anhydrous CH$_2$Cl$_2$ dropwise. After 10 minutes, Compound 11 (78 mg, 0.190 mmol) in 12 mL of anhydrous CH$_2$Cl$_2$ was added dropwise. After the addition, the reaction mixture was allowed to warm slowly to −10° C. over 2 hours. The reaction was quenched with the addition of saturated aqueous NH$_4$Cl and extracted with EtOAc. The organic layer was washed with saturated aqueous NaCl, dried over Na$_2$SO$_4$, and concentrated under reduced pressure. The residue was purified by PTLC (SiO$_2$, 50% EtOAc/hexanes elution) providing Compound 12 (12.7 mg, 17%) as a bright yellow solid. $^1$H NMR (acetone-d$_6$, 600 MHz) δ 7.99 (d, J=8.4 Hz, 1H), 7.82 (d, J=7.2 Hz, 1H), 7.77 (br, 1H), 6.63 (t, J=7.8 Hz, 1H), 4.21 (m, 2H), 4.14 (m, 1H), 4.00 (dd, J=11.1, 3.6 Hz, 1H), 3.79 (dd, J=8.4, 11.4 Hz, 1H), 3.56 (s, 3H), 1.58 (s, 9H). $^{13}$C NMR (acetone-d$_6$, 150 MHz) δ 161.8, 153.7, 153.3, 144.8, 131.2, 130.0, 127.9, 123.9, 121.6, 118.5, 118.1, 99.2, 82.7, 54.7, 48.7, 45.5, 36.2, 29.5. IR (film) ν$_{max}$ 2978, 1702, 1404, 1141 cm$^{-1}$. ESI-TOF HRMS m/z 389.1268 (M+H$^+$, C$_{20}$H$_{21}$ClN$_2$O$_4$ requires 389.1263).

The enantiomers were resolved on a semi-preparative Diacel ChiralCel® OD column (0.46 cm×25 cm) with 5% i-PrOH/hexanes elution. α=1.14

(1S)-12: [α]$^{23}_D$ −35 (c 1.22, THF), natural enantiomer.
(1R)-12: [α]$^{23}_D$ +40 (c 0.42, THF), unnatural enantiomer.

N-(2-(10-(Chloromethyl)-5-methyl-4-oxo-5,8,9,10-tetrahydro-4H-pyrrolo[3',2':5,6]naphtho[1,8-de][1,2]oxazine-8-carbonyl)-1H-indol-5-yl)-1H-indole-2-carboxamide (Compound 6)

N-Methyl oxazinane Compound 12 (6.8 mg, 0.017 mmol) was dissolved in 4 N HCl in EtOAc (0.5 mL) and the mixture was allowed to stir at room temperature for 15 minutes. The solvent was removed under a stream of nitrogen and the residue was redissolved in anhydrous DMF (0.34 mL). EDCI (10.0 mg, 0.052 mmol) and Compound 16 (6.1 mg, 0.019 mmol) were added and the reaction mixture was allowed to stir at 25° C. for 20 hours. The reaction mixture was quenched with the addition H$_2$O and diluted with EtOAc. The organic phase was washed with 2 N aqueous HCl (3×), saturated aqueous NaHCO$_3$ (5×) and saturated aqueous NaCl. The organic extract was dried over Na$_2$SO$_4$ and concentrated under reduced pressure. The residue was purified by PTLC (SiO$_2$, 40% THF/toluene) providing Compound 6 (5.7 mg, 56%) as a yellow solid. $^1$H NMR (DMSO-d$_6$, 600 MHz) δ 11.84 (s, 1H), 11.73 (s, 1H), 10.18 (s, 1H), 8.25 (s, 1H), 8.21 (d, J=7.8 Hz, 1H), 8.09 (br, 1H), 7.90 (d, J=7.2 Hz, 1H), 7.74 (t, J=8.4 Hz, 1H), 7.68 (d, J=8.4 Hz, 1H), 7.59 (d, J=9.0 Hz, 1H), 7.50-7.47 (m, 2H), 7.43 (s, 1H), 7.29 (s, 1H), 7.21 (t, J=8.4 Hz, 1H), 7.07 (t, J=7.2 Hz, 1H), 4.91 (t, J=9.6 Hz, 1H), 4.65 (dd, J=11.4, 2.4 Hz, 1H), 4.39 (m, 1H), 4.09-4.04 (m, 1H), 4.03-4.01 (m, 1H), 3.58 (s, 3H). $^{13}$C NMR (DMSO-d$_6$, 150 MHz) 160.3, 159.5, 159.4, 150.1, 142.9, 136.6, 133.4, 131.77, 131.70, 130.6, 128.5, 128.4, 127.04, 127.02, 126.9, 123.4, 121.5, 121.3, 120.5, 119.7, 119.5, 118.2, 117.0, 112.8, 112.27, 112.24, 106.2, 103.3, 98.9, 54.9, 47.5, 40.7, 34.9. ESI-TOF HRMS m/z 590.1592 (M+H$^+$, C$_{33}$H$_{24}$ClN$_5$O$_4$ requires 590.1589).

(1S)-6: [α]$^{23}_D$ +54 (c 0.38, THF), natural enantiomer.
(1R)-6: [α]$^{23}_D$ −57 (c 0.24, THF), unnatural enantiomer.

tert-Butyl 10-(Chloromethyl)-4-oxo-9,10-dihydro-4H-pyrrolo[3',2':5,6]naphtho[1,8-de][1,2]oxazine-8(5H)-carboxylate (Compound 15)

The carboxylic acid Compound 9 (191 mg, 0.41 mmol) in anhydrous THF (2.0 mL) at 25° C. was treated with CDMT (78.0 mg, 0.45 mmol) and NMM (134 µL, 1.22 mmol). After 2 hours, NH$_2$OH—HCl (31 mg, 0.45 mmol) in 2.0 mL of DMF was added and the reaction mixture was stirred for 6 hours. After 6 hours, the reaction mixture was quenched with the addition of H$_2$O and extracted with EtOAc (3×). The organic layers were combined, washed with 2 N aqueous HCl, saturated aqueous NaCl, dried over Na$_2$SO$_4$, and concentrated under reduced pressure. The residue was purified by PTLC (SiO$_2$, 50% EtOAc/hexanes elution) providing the hydroxamic acid (130 mg, 93% BRSM) as a light brown foam. ESI-TOF HRMS m/z 483.1677 (M+H$^+$, C$_{26}$H$_{27}$ClN$_2$O$_5$ requires 483.1681).

The hydroxamic acid (130 mg) was dissolved in anhydrous CH$_3$OH (3.36 mL) under Ar. 10% Pd/C (28.6 mg, 0.026 mmol) was added and the atmosphere was exchanged with H$_2$. The reaction mixture was allowed to stir at 25° C. for 50 minutes. The reaction mixture was diluted with Et$_2$O, filtered through Celite®, and concentrated under reduced pressure. The residue was purified by PTLC (SiO$_2$, EtOAc elution) providing Compound 13 (46 mg, 56% BRSM) as an orange foam. ESI-TOF HRMS m/z 393.1208 (M+H$^+$, C$_{19}$H$_{21}$ClN$_2$O$_5$ requires 393.1212).

A stirred solution of (COCl)$_2$ (14.7 µL, 0.175 mmol) in anhydrous CH$_2$Cl$_2$ (3 mL) at −78° C. was treated with Me$_2$SO (27.3 µL, 0.351 mmol) in 2 mL of anhydrous CH$_2$Cl$_2$ dropwise. After 10 minutes, Compound 13 (46 mg, 0.117 mmol) in 6 mL of anhydrous CH$_2$Cl$_2$ was added dropwise. After the addition, the reaction mixture was allowed to warm slowly to −10° C. over 2 hours. The reaction mixture was quenched with the addition of saturated aqueous NH$_4$Cl and extracted with EtOAc. The organic layer was washed with saturated aqueous NaCl, dried over Na$_2$SO$_4$, and concentrated under reduced pressure. The residue was purified by PTLC (SiO$_2$, 50% EtOAc/hexanes elution) yielding Compound 15 (9 mg, 27%) as a tan solid. $^1$H NMR (acetone-d$_6$, 600 MHz) δ 8.04 (d, J=9 Hz, 1H), 7.80 (d, J=7.2 Hz, 1H), 7.79 (br, 1H), 7.66 (t, J=7.2 Hz, 1H), 4.22-4.16 (m, 3H), 4.01 (dd, J=11.1, 3.6 Hz, 1H), 3.79 (dd, J=8.1, 11.4 Hz, 1H), 1.57 (s, 9H). $^{13}$C NMR (THF-d$_8$, 150 MHz) δ 161.9, 153.5, 152.8, 144.2, 130.5, 129.0, 126.5, 122.4, 118.9, 118.3, 116.1, 98.0, 81.6, 53.9, 47.3, 42.3, 28.6. IR (film) ν$_{max}$ 2920, 1660, 1409, 1139, 758 cm$^{-1}$. ESI-TOF HRMS m/z 375.1120 (M+H$^+$, C$_{19}$H$_{19}$ClN$_2$O$_4$ requires 375.1106).

The enantiomers were resolved on a semi-preparative Diacel ChiralCel® OD column (0.46 cm×25 cm) with 15% i-PrOH/hexanes elution. α=1.19.

(1S)-15: [α]$^{23}_D$ −17 (c 0.39, THF), natural enantiomer.
(1R)-15: [α]$^{23}_D$ +19 (c 0.30, THF), unnatural enantiomer.

Perfluorophenyl 5-(1H-Indole-2-carboxamido)-1H-indole-2-carboxylate (Compound 17)

Compound 16 (20 mg, 0.062 mmol), C$_6$F$_5$OH (17.2 mg, 0.093 mmol), and EDCI (35.5 mg, 0.186 mmol) were combined, suspended in DMF (0.62 mL), and the mixture was stirred at 25° C. for 3 hours. The reaction mixture was diluted with EtOAc and washed with H$_2$O. The organic layers was dried over Na$_2$SO$_4$ and concentrated under reduced pressure. Compound 17 (25 mg, 83%) was isolated as a tan solid. $^1$H NMR (DMSO-d$_6$, 600 MHz) δ 12.44 (s, 1H), 11.72 (s, $^1$H), 10.24 (s, 1H), 8.29 (s, 1H), 7.74 (dd, J=10.8, 1.8 Hz, 1H), 7.68 (d, J=8.4 Hz, 1H), 7.62 (d, J=1.8 Hz, 1H), 7.53 (d, J=9.0 Hz, 1H), 7.48 (d, J=8.4 Hz, 1H), 7.43 (d, J=1.2 Hz, 1H), 7.22 (t, J=7.9 Hz, 1H), 7.08 (t, J=7.8 Hz, 1H). $^{13}$C NMR (DMSO-d$_6$, 150 MHz) δ 159.5, 156.9, 141.6, 139.9, 138.3, 136.6, 135.6, 132.5, 131.6, 127.0, 126.4, 124.2, 123.5, 123.2, 121.6, 121.5, 119.7, 112.89, 112.88, 112.2, 111.9, 103.4. IR (film) $v_{max}$ 3360, 3256, 1721, 1646, 1515, 994 cm$^{-1}$. ESI-TOF HRMS m/z 486.0890 (M+H$^+$, C$_{24}$H$_{12}$F$_5$N$_3$O$_3$ requires 486.0872).

N-(2-(10-(Chloromethyl)-4-oxo-5,8,9,10-tetrahydro-4H-pyrrolo[3',2':5,6]naphtho[1,8-de][1,2]oxazine-8-carbonyl)-1H-indol-5-yl)-1H-indole-2-carboxamide (Compound 7)

Compound 15 (3.2 mg, 0.008 mmol) was dissolved in 4 N HCl in EtOAc (0.3 mL) and the mixture was allowed to stir at room temperature for 10 minutes. The solvent was removed under a stream of nitrogen and the residue was redissolved in anhydrous DMF (0.2 mL). Et$_3$N (5.9 µL, 0.042 mmol) and Compound 17 (4.9 mg, 0.010 mmol) were added and the reaction mixture was allowed to stir at 25° C. for 20 hours. The reaction mixture was quenched with the addition of H$_2$O and diluted with EtOAc. The organic phase was washed with saturated aqueous NaCl, dried over Na$_2$SO$_4$, and concentrated under reduced pressure. The residue was purified by PTLC (SiO$_2$, 40% THF/toluene) providing Compound 7 (1.07 mg, 22%) as a yellow solid. $^1$H NMR (DMSO-d$_6$, 600 MHz) δ 11.83 (s, 1H), 11.73 (s, 1H), 10.18 (s, 1H), 8.24 (s, 1H), 8.16 (br, 1H), 8.02 (br, 1H), 7.71 (br, 1H), 7.68 (d, J=18 Hz, 1H), 7.59 (dd, J=9.3, 2.4 Hz, 1H), 7.49-7.46 (m, 2H), 7.43 (s, 1H), 7.28 (s, 1H), 7.21 (t, J=6.6 Hz, 1H), 7.07 (t, J=7.8 Hz, 1H), 4.89 (t, J=9 Hz, 1H), 4.64 (d, J=9.6 Hz, 1H), 4.35 (br, 1H), 4.08-3.99 (m, 2H). $^{13}$CNMR (DMSO-d$_6$, 150 MHz) 161.9, 160.3, 159.4, 143.2, 136.6, 133.4, 131.8, 131.7, 130.8, 128.6, 128.4, 127.9, 127.0, 124.8, 123.5, 121.6, 119.8, 119.5, 118.3, 112.8, 112.3, 112.2, 106.9, 106.1, 103.3, 98.7, 66.9, 66.5, 54.9, 47.3, 40.7 δ. ESI-TOF HRMS m/z 576.1423 (M+H$^+$, C$_{32}$H$_{22}$ClN$_5$O$_4$ requires 576.1433).

(1S)-7: [α]$^{23}_D$ +18 (c 0.06, acetone), natural enantiomer.
(1R)-7: [α]$^{23}_D$ −16 (c 0.07, acetone), unnatural enantiomer.

tert-Butyl 1,2-Dihydro-1-(chloromethyl)-5-hydroxy-6-(methylcarbamoyl)benzo[e]indole-3-carboxylate (Compound 18)

$^1$H NMR (acetone-d$_6$, 600 MHz) δ 10.66 (s, 1H), 8.26 (s, 1H), 7.96 (d, J=7.8 Hz, 1H), 7.74 (br, 1H), 7.56 (d, J=7.2 Hz, 1H), 7.46 (t, J=7.8 Hz, 1H), 4.21 (d, J=11.4 Hz, 1H), 4.14-4.09 (m, 2H), 3.95 (d, J=10.8 Hz, 1H), 3.68 (t, J=9.6 Hz, 1H), 3.01 (s, 3H), 1.58 (s, 9H). $^{13}$C NMR (DMSO-d$_6$, 150 MHz) δ 171.5, 154.7, 151.5, 141.7, 135.5, 130.6, 126.1, 123.1, 122.2, 117.0, 113.3, 99.6, 80.2, 52.3, 47.6, 40.2, 28.0, 26.1. IR (film) $v_{max}$ 2924, 1697, 1615, 1539, 1403, 1327, 1137, 760 cm$^{-1}$. ESI-TOF HRMS m/z 391.1422 (M+H$^+$, C$_{20}$H$_{23}$ClN$_2$O$_4$ requires 391.1419).

3-(5-(1H-Indole-2-carboxamido)-1H-indole-2-carbonyl)-1-(chloromethyl)-5-hydroxy-N-methyl-1,2-dihydrobenzo-[e]indole-6-carboxamide (Compound 19)

Compound 18 (15 mg, 0.038 mmol) was dissolved in 4 N HCl in EtOAc (1 mL) and the mixture was allowed to stir at room temperature for 15 minutes. The solvent was removed under a stream of nitrogen and the residue was redissolved in anhydrous DMF (0.76 mL). EDCI (21.9 mg, 0.115 mmol) and Compound 16 (14.6 mg, 0.045 mmol) were added and the reaction mixture was allowed to stir at 25° C. for 22 hours. The reaction mixture was quenched with the addition of H$_2$O and diluted with EtOAc. The organic phase was washed with 2 N aqueous HCl (3×), saturated aqueous NaHCO$_3$ (5×) and saturated aqueous NaCl. The organic extract was dried over Na$_2$SO$_4$ and concentrated under reduced pressure. The residue was purified by PTLC (SiO$_2$, 40% THF/toluene) providing Compound 19 (7.1 mg, 31%) as a dark yellow solid. $^1$H NMR (DMSO-d$_6$, 600 MHz) δ 11.74 (d, J=16.2 Hz, 2H), 10.48 (s, 1H), 10.18 (s, 1H), 8.24 (s, 1H), 8.07-8.06 (m, 1H), 7.95 (br, 1H), 7.90 (d, J=7.8 Hz, 1H), 7.68 (d, J=7.8 Hz, 1H), 7.59 (d, J=9 Hz, 1H), 7.50-7.47 (m, 2H), 7.43 (s, 1H), 7.24-7.18 (m, 3H), 7.07 (t, J=7.8 Hz, 1H), 4.84 (t, J=10.2 Hz, 1H), 4.59 (d, J=10.8 Hz, 1H), 4.28 (m, 1H), 4.01 (d, J=9 Hz, 1H), 3.88 (dd, J=7.2, 10.8 Hz, 1H), 2.77 (s, 3H). $^{13}$C NMR (DMSO-d$_6$, 150 MHz) δ 171.2, 159.7, 159.1, 154.0, 142.2, 136.3, 135.3, 132.9, 131.5, 131.2, 130.8, 130.0, 126.74, 126.72, 125.9, 123.3, 123.1, 122.7, 121.2, 119.4, 118.9, 117.7, 114.9, 112.5, 112.0, 111.8, 105.4, 103.0, 101.4, 54.5, 47.3, 40.8, 25.9. IR (film) $v_{max}$ 3293, 2953, 1613, 1516, 1402, 1241, 1138 cm$^{-1}$. ESI-TOF HRMS m/z 592.1744 (M+H$^+$, C$_{33}$H$_{26}$ClN$_5$O$_4$ requires 592.1746).

3-(5-(1H-indole-2-carboxamido)-1H-indole-2-carbonyl)-1-(chloromethyl)-5-hydroxy-N-methyl-2,3-dihydro-1H-benzo[e]indole-6-carboxamide (Compound 20)

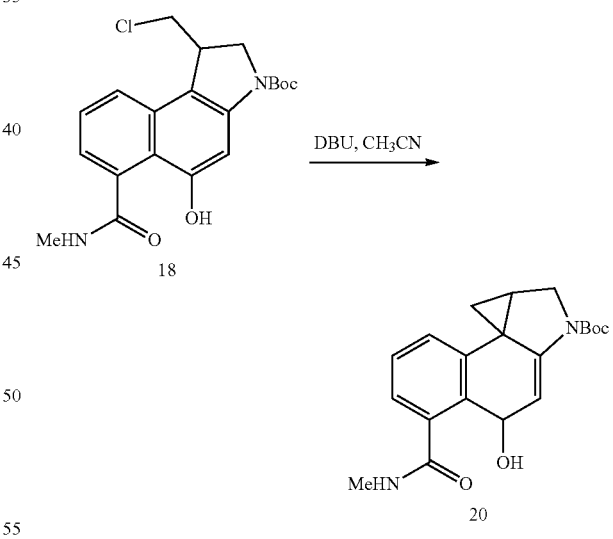

Compound 18 (11.3 mg, 28 µmol) in 0.6 mL of acetonitrile was treated with 1,8-diazabicyclo-[5.4.0]undec-7-ene (DBU, 12.9 µL, 0.086 mmol). The reaction mixture was allowed to stir a room temperature for 90 minutes. After 90 minutes, the solvent was evaporated under reduced pressure and the residue was purified by PTLC (SiO$_2$, EtOAc) to provide Compound 20 (1.5 mg, 15% yield) as a yellow foam. $^1$H NMR (acetone-d$_6$, 600 MHz) δ 7.48 (t, J=7.8 Hz, 1H), 7.18 (d, J=7.2 Hz, 1H), 7.08 (d, J=7.8 Hz, 1H), 6.78 (br, 1H), 6.65 (br, 1H) 4.05-3.99 (m, 2H), 3.03 (m, 1H), 2.86 (d, J=4.8 Hz, 3H), 1.64 (dd, J=7.2, 4.2 Hz, 1H), 1.52 (s, 9H), 1.49 (t, J=4.2 Hz, 1H). $^{13}$C NMR (acetone-$d_6$, 150 MHz) δ 185.5, 172.6, 153.1, 142.7, 140.7, 132.6, 131.3, 127.5, 123.8, 109.5, 101.2, 83.8, 54.5, 35.0, 33.3, 29.0, 27.5, 25.4. ESI-TOF HRMS m/z 355.1656 (M+H$^+$, $C_{20}H_{22}N_2O_4$ requires 355.1652).

DNA Alkylation Studies

See Boger et al., *Tetrahedron* 1991, 47:2661-2682 for full details of the DNA alkylation assay. The DNA alkylation reactions were conducted at 25° C. with 5'-$^{32}$P-end-labeled w794 DNA, which contains a single major alkylation site for the natural products. The glutathione reductive activation of Compounds (+)-7 and (+)-3c was conducted for the specified time with 1 M L-glutathione at 37° C.

Cell Growth Inhibition Assay

Compounds were tested for their cell growth inhibition of L1210 (ATCC CCL-219) mouse lymphocytic leukemia cells. A population of cells (>1×10$^6$ cells/mL as determined with a hemocytometer) was diluted with an appropriate amount of Dulbecco-modified Eagle Medium (DMEM, Gibco) containing 10% fetal bovine serum (FBS, Gibco) to a final concentration of 30,000 cells/mL. To each well of a 96-well plate (Corning® Costar®), 100 µL of the cell-media solution was added with a multichannel pipette. The cultures were incubated at 37° C. in an atmosphere of 5% CO$_2$ and 95% humidified air for 24 hours. The test compounds were added to the plate as follows: test substances were diluted in DMSO to a concentration of 1 mM and 10-fold serial dilutions were performed on a separate 96-well plate. Fresh culture medium (100 µL) was added to each well of cells to constitute 200 µL of medium per well followed by 2 µL of each test agent. Compounds were tested in duplicate (≥2 times) at six concentrations between 0-100 nM or 0-1000 nM. Following addition, cultures were incubated for an additional 72 hours.

A phosphatase assay was used to establish the IC$_{50}$ values as follows: the media in each cell was removed and 100 µL of phosphatase solution (100 mg phosphatase substrate in 30 mL 0.1 M NaOAc, pH 5.5, 0.1% Triton® X-100 buffer) was added to each well. The plates were incubated at 37° C. for 5 minutes. After the given incubation time, 50 µL of 0.1 N NaOH was added to each well and the absorption at 405 nm was determined using a 96 well plate reader. As the absorption is directly proportional to the number of living cells, the IC$_{50}$ values were calculated and the reported values represent of the average of ≥4 determinations (SD±10%).

In Vivo Antitumor Activity

B6D2F1 mice were injected intraperitoneally (i.p.) with syngeneic L1210 cells (1×10$^6$) on day 0. Ten mice were randomly assigned to control vehicle or treatment groups for Compounds (+)-4 and (+)-6 at doses of 60, 100, 250, and 500 µg/kg/inj for Compounds (+)-4 or 60, 200, 500, 1000, and 2500 µg/kg/inj for Compounds (+)-6. Compounds (+)-4 and (+)-6 were formulated in 100% DMSO. Both compounds were injected i.p. on days 1, 5, and 9. Following injection of tumor cells, animals were monitored daily and weighed two times per week. Percent survival (T/C) for treated and control groups were determined by dividing the total survival days for each treatment group by the total survival days for the control group and multiplying×100. All animal studies were carried out in the animal facilities of The University of Kansas Medical Center with strict adherence to the guidelines of the IACUC Animal Welfare Committee of KUMC (IACUC approval #2009-1837).

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A cyclic N-acyl O-amino phenol CBI derivative represented by Formula I:

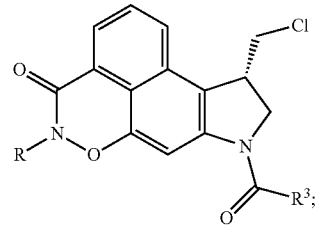

Formula I wherein:
R is hydrido or a $C_1$-$C_6$ hydrocarbyl; and
R$^3$ is selected from group consisting of radicals represented as follows:

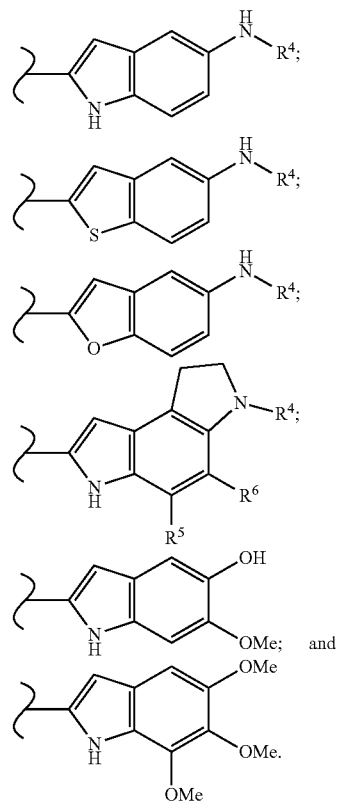

wherein:
R$^4$ is selected from group consisting of radicals represented as follows:

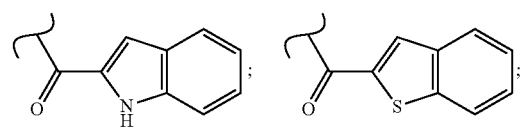

-continued

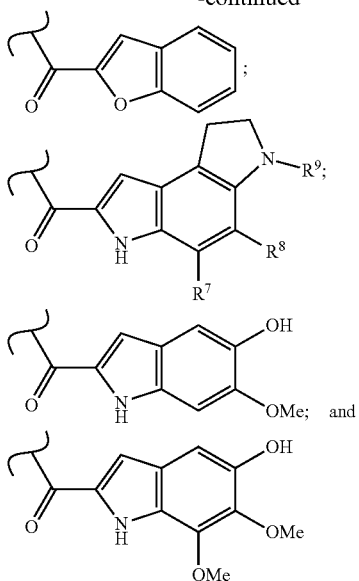

R⁵, R⁶, R⁷ and R⁸ are each independently selected from the group of radicals consisting of —H, —OH, —O(C₁-C₆ hydrocarbyl), C₁-C₆ hydrocarbyl and halogen; and R⁹ is selected from the group of radicals consisting of —H, —C(O)O'(C₁-C₆ hydrocarbyl), —C(O)(C₁-C₆ hydrocarbyl), —C(O)NH₂, —C(O)NHNH₂, and —C(O)NHNHC(O)O(C₁-C₆ hydrocarbyl).

2. The cyclic N-acyl O-amino phenol CBI derivative according to claim 1, wherein R is hydrido or methyl.

3. The cyclic N-acyl O-amino phenol CBI derivative according to claim 1, wherein R³ is one or the other of the following radicals:

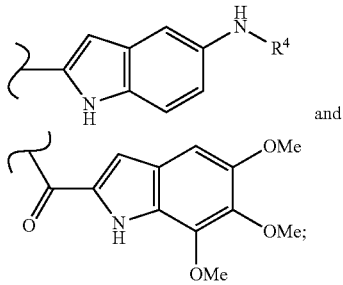

R⁴ is one or the other of the following radicals

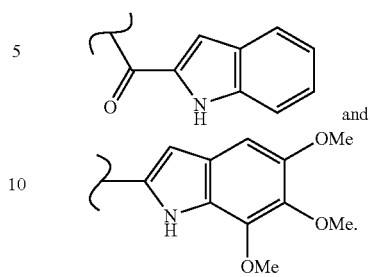

4. The cyclic N-acyl O-amino phenol CBI derivative according to claim 1 that is represented by the formula

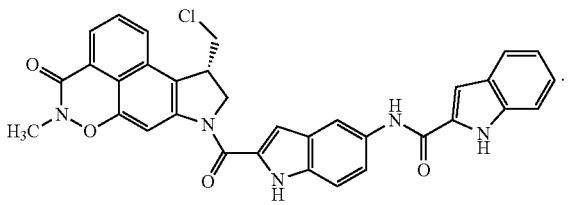 [SMILES: CN1Oc2cc3c(c4cccc(c24)C1=O)[C@H](CCl)CN3C(=O)c1cc2cc(NC(=O)c3cc4ccccc4[nH]3)ccc2[nH]1]

5. The cyclic N-acyl O-amino phenol CBI derivative according to claim 1 that is represented by the formula

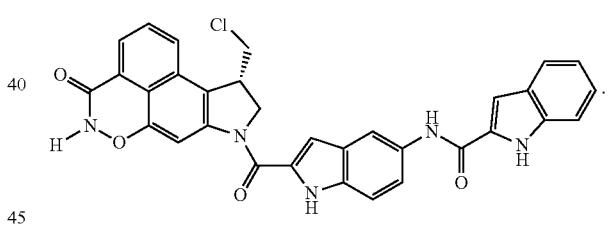

6. The cyclic N-acyl O-amino phenol CBI derivative according to claim 1 that is represented by a formula selected from the group consisting of one or more of

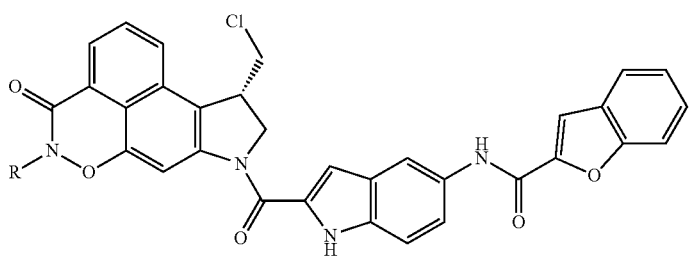

-continued
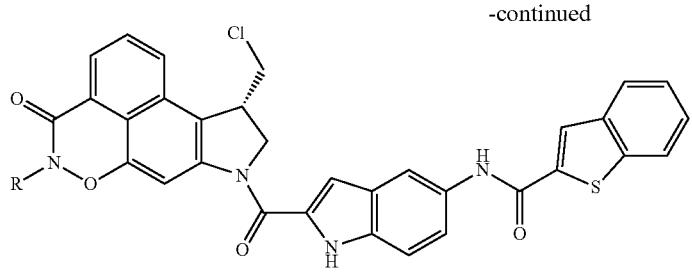
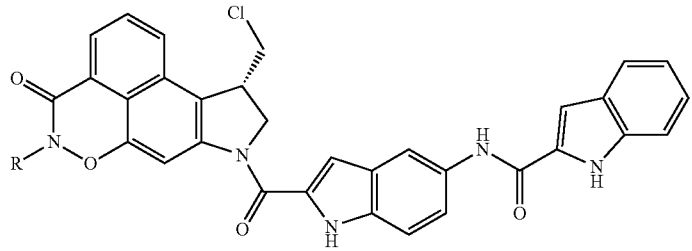
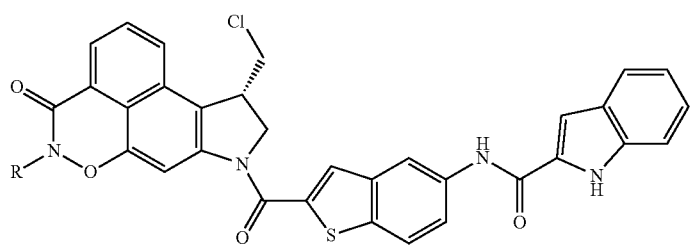
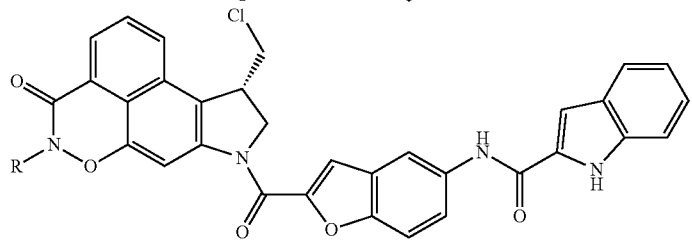
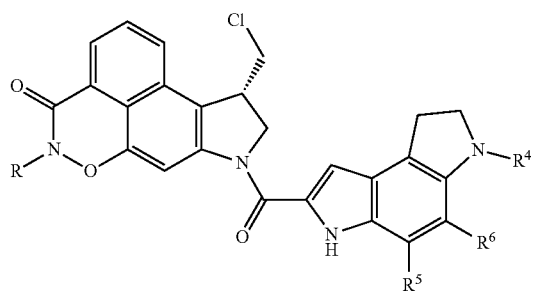
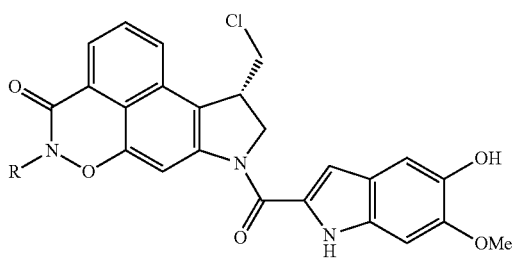
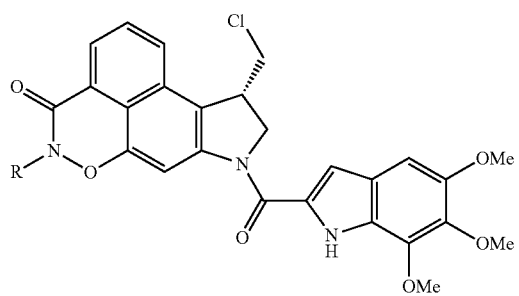

-continued
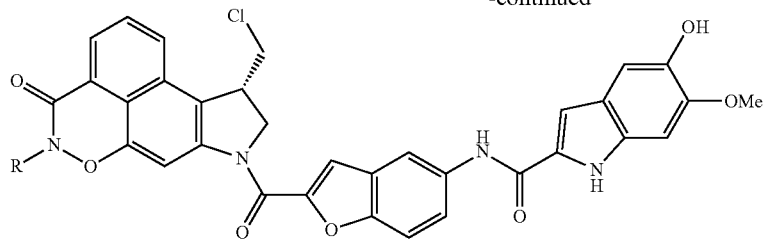
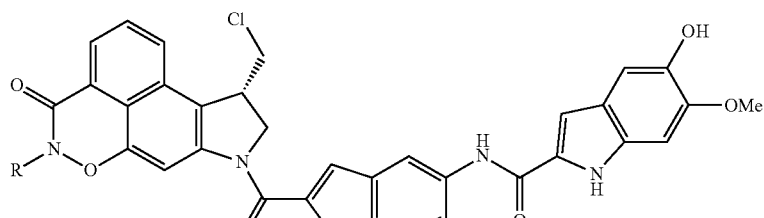
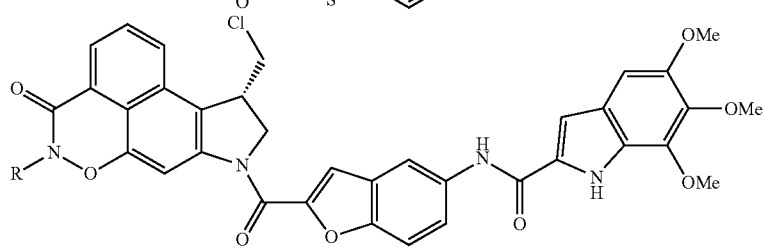
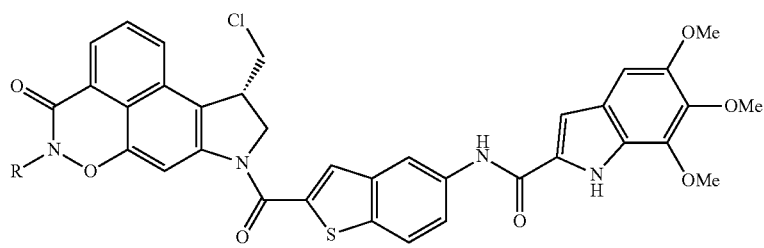
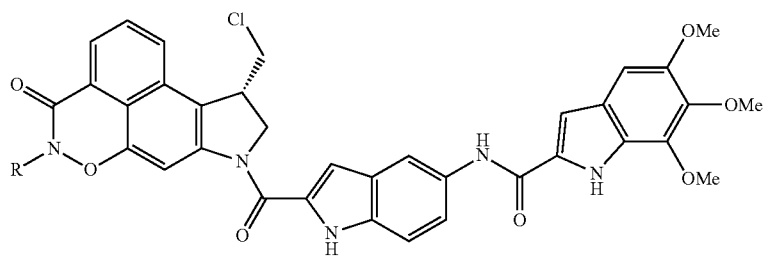
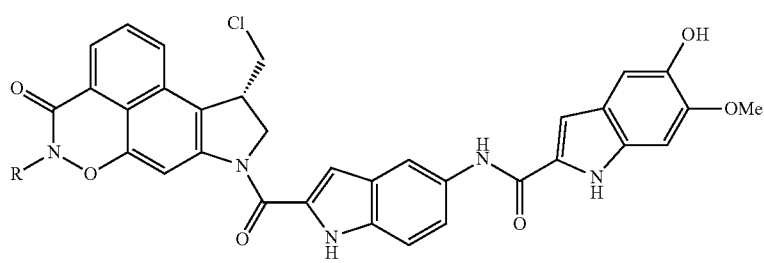
wherein R, R⁴, R⁵ and R⁶ are as defined in claim 1.

7. A pharmaceutical composition comprising a proliferative disease-inhibiting amount of a compound of claim 1 dissolved or dispersed in a pharmaceutically acceptable diluent.

8. The composition according to claim 7, wherein said compound is one or the other or both of

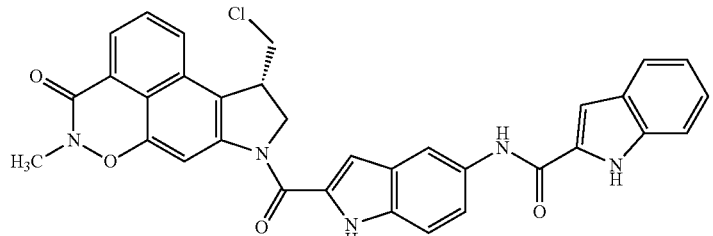

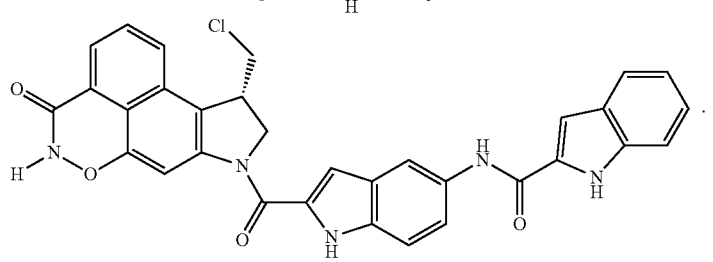

and

.

9. A process for treating a cancer or leukemia disease in a mammal comprising the step of administering an effective amount of a compound of claim 1 to said mammal in need thereof.

10. The process according to claim 9, wherein said disease is leukemia.

11. The process according to claim 9, wherein said compound is one or the other or both of

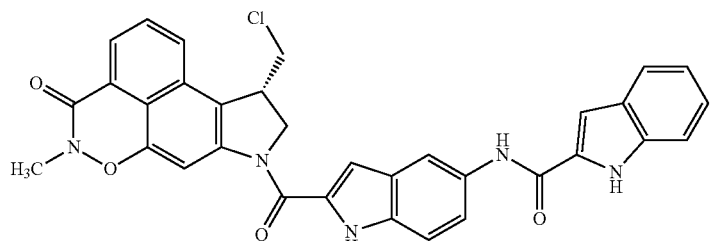

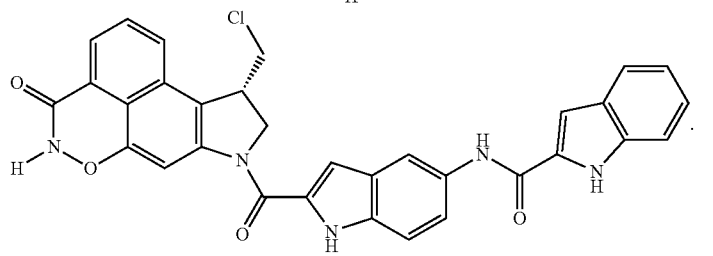

and

.

* * * * *

UNITED STATES PATENT AND TRADEMARK OFFICE
CERTIFICATE OF CORRECTION

| | | |
|---|---|---|
| PATENT NO. | : 9,586,974 B2 | Page 1 of 1 |
| APPLICATION NO. | : 14/773257 | |
| DATED | : March 7, 2017 | |
| INVENTOR(S) | : Dale L. Boger | |

It is certified that error appears in the above-identified patent and that said Letters Patent is hereby corrected as shown below:

In the Specification

Column 1, Lines 10-15, the paragraph GOVERNMENTAL SUPPORT should be changed to:
-- STATEMENT OF GOVERNMENT LICENSE RIGHTS
This invention was made with government support under grant number CA041986 awarded by the National Institutes of Health. The government has certain rights in the invention. --

Signed and Sealed this
Fifth Day of May, 2020

Andrei Iancu
*Director of the United States Patent and Trademark Office*